US008410061B2

(12) United States Patent
Williams et al.

(10) Patent No.: US 8,410,061 B2
(45) Date of Patent: *Apr. 2, 2013

(54) FUNCTIONAL ANTAGONISTS OF HEDGEHOG ACTIVITY

(75) Inventors: Kevin Williams, Chapel Hill, NC (US);
Paul Rayhorn, Foxborough, MA (US);
Ellen A. Garber, Cambridge, MA (US);
R. Blake Pepinsky, Arlington, MA (US)

(73) Assignee: Curis. Inc., Lexington, MA (US)

( * ) Notice: Subject to any disclaimer, the term of this patent is extended or adjusted under 35 U.S.C. 154(b) by 759 days.

This patent is subject to a terminal disclaimer.

(21) Appl. No.: 10/164,282

(22) Filed: Jun. 5, 2002

(65) Prior Publication Data

US 2003/0166543 A1   Sep. 4, 2003

Related U.S. Application Data

(63) Continuation of application No. 09/890,975, filed as application No. PCT/US99/25700 on Nov. 2, 1999, now abandoned.

(60) Provisional application No. 60/106,703, filed on Nov. 2, 1998.

(51) Int. Cl.
*A61K 38/17* (2006.01)

(52) U.S. Cl. ............... 514/21.3; 514/19.3; 514/20.7; 530/350

(58) Field of Classification Search ............ None
See application file for complete search history.

(56) References Cited

U.S. PATENT DOCUMENTS

| | | | |
|---|---|---|---|
| 5,759,811 A | 6/1998 | Epstein et al. | |
| 5,789,543 A | 8/1998 | Ingham et al. | |
| 5,844,079 A * | 12/1998 | Ingham et al. | 530/350 |
| 6,165,747 A | 12/2000 | Ingham et al. | |
| 6,261,786 B1 | 7/2001 | Marigo et al. | |
| 6,271,363 B1 | 8/2001 | Ingham et al. | |
| 6,384,192 B1 | 5/2002 | Ingham et al. | |
| 6,444,793 B1 * | 9/2002 | Pepinsky et al. | 530/402 |
| 6,576,237 B1 | 6/2003 | Ingham et al. | |
| 6,607,913 B1 | 8/2003 | Ingham et al. | |
| 6,610,656 B1 | 8/2003 | Ingham et al. | |
| 6,630,148 B1 | 10/2003 | Ingham et al. | |
| 6,639,051 B2 | 10/2003 | Wang | |
| 6,664,075 B2 | 12/2003 | Ingham et al. | |
| 6,767,888 B1 * | 7/2004 | Mahanthappa | 514/2 |
| 6,884,775 B1 | 4/2005 | Tabin et al. | |
| 6,897,297 B1 * | 5/2005 | Pepinsky et al. | 530/402 |
| 7,060,450 B1 | 6/2006 | Tabin et al. | |
| 7,144,732 B2 | 12/2006 | Ingham et al. | |
| 7,445,778 B2 | 11/2008 | Burkly et al. | |
| 2004/0038876 A1 | 2/2004 | Pepinsky et al. | |
| 2005/0119181 A1 | 6/2005 | Pepinsky et al. | |

FOREIGN PATENT DOCUMENTS

| | | |
|---|---|---|
| WO | WO 95/23223 | 8/1995 |
| WO | WO 98/12326 | 3/1998 |
| WO | WO 99/05989 | 2/1999 |
| WO | WO 99/20298 | 4/1999 |
| WO | WO 00/18428 * | 4/2000 |

OTHER PUBLICATIONS

Tanaka Hall et al., Nature, 1995, vol. 378, pp. 212-216.*
Pepinsky et al., J. of Bio. Chem., 1998, vol. 273, No. 22, pp. 14037-14045.*
Alcedo, J. et al. The *Drosophila* smoothened Gene Encodes a Seven-Pass Membrane Protein, a Putative Receptor for the Hedgehog Signal. Cell 86, 221-232 (Jul. 26, 1996).
Alexandre, C. et al. Transcriptional activation of hedgehog target genes in *Drosophila* is mediated directly by the Cubitus interrutus protein, a member of the GLI family of zinc finger DNA-binding proteins. Genes Dev. 10, 2003-2013 (1996).
Bumcrot, D.A. et al. Proteolytic Processing Yields Two Secreted Forms of Sonic hedgehog. Mol. Cell Biol. 15, 2294-2303 (Apr. 1995).
Chang, D.T. et al. Products, genetic linkage and limb patterning activity of a murine hedgehog gene. Development 120, 3339-3353 (1994).
Dominguez, M. et al. Sending and Receiving the Hedgehog Signal: Control by the *Drosophila* Gli Protein Cubitus interruptus. Science 272, 1621-1625 (Jun. 14, 1996).
Echelard, Y. et al. Sonic Hedgehog, a Member of a Family of Putative Signaling Molecules, Is Implicated in the Regulation of CNS Polarity. Cell 75, 1417-1430 (Dec. 31, 1993).
Ekker, S.C. et al. Patterning activities of vertebrate hedgehog proteins in the developing eye and brain. Current Biol. 5, 944-955 (1995).
Fan, C.-M. et al. Long-Range Sclerotome Induction by Sonic Hedgehog: Direct Role of the Amino-Terminal Cleavage Product and Modulation by the Cyclic AMP Signaling Pathway. Cell 81, 457-465 (1995).
Hall, T.M.T. et al. A potential catalytic site revealed by the 1.7-A crystal structure of the amino-terminal signaling domain of Sonic hedgehog. Nature 378, 212-216 (Nov. 9, 1995).
Iseki, S. et al. Sonic Hedgehog is Expressed in Epithelial Cells during Development of Whisker, Hair, and Tooth. Biochem. Biophys. Res. Comm. 218, 688-693 (1996).
Johnson, R.L. and Tabin, C. The Long and Short of hedgehog Signaling. Cell 81, 313-316 (May 5, 1995).
Katsuura, M. et al. The NH2-terminal region of the active domain of sonic hedgehog is necessary for its signal transduction. Febs. Lett. 447, 325-328 (Mar. 26, 1999).
Lee, J.J. et al. Autoproteolysis in hedgehog Protein Biogenesis. Science 266, 1528-1536 (1994).

(Continued)

*Primary Examiner* — Christopher R Tate
*Assistant Examiner* — Roy Teller
(74) *Attorney, Agent, or Firm* — Ropes & Gray LLP

(57) ABSTRACT

Variants of hedgehog protein that contain N-terminal modifications are described that can block hedgehog function; thus allowing these variants to serve as functional antagonists. These peptides have a primary amino acid sequence lacking the ability to elicit a hedgehog-dependent response in C3H 10T1/2 cells but having the ability to bind to the hedgehog receptor, patched-1. Methods for producing such functional antagonists and methods of using the functional antagonists are also described.

41 Claims, 4 Drawing Sheets

OTHER PUBLICATIONS

Marigo, V. et al. Biochemical evidence that Patched is the Hedgehog receptor. Nature 384, 176-179 (1996).

Mohler, J. and Vani, K. Molecular organization and embryonic expression of the hedgehog gene involved in cell-cell communication in segmental patterning of *Drosophila*. Development 115, 957-971 (1992).

Nakamura, T. et al. Induction of Osteogenic Differentiation by Hedgehog Proteins. Biochem. Biophys. Res. Comm. 237, 465-469 (1997).

Pepinsky, R.B. et al. Identification of a Palmitic Acid-modified Form of Human Sonic hedgehog. J. Biol. Chem. 273, 14037-14045 (May 29, 1998).

Perrimon, N. Hedgehog and Beyond. Cell 80, 517-520 (Feb. 24, 1995).

Porter, J.A. et al. Hedgehog Patterning Activity: Role of a Lipophilic Modification Mediated by the Carboxy-Terminal Autoprocessing Domain. Cell 86, 21-34 (Jul. 12, 1995).

Porter, J.A. et al. The product of hedgehog autoproteolytic cleavage active in local and long-range signaling. Nature 374, 363-366 (Mar. 23, 1995).

Porter, J.A. et al. Cholesterol Modification of Hedgehog Signaling Proteins in Animal Development. Science 274, 255-258 (Oct. 11, 1996).

Riddle, R.D. et al. Sonic hedgehog Mediates the Polarizing Activity of the ZPA. Cell 75, 1401-1416 (Dec. 31, 1993).

Roelink, H. et al. Floor Plate and Motor Neuron Induction by vhh-1, a Vertebrate Homolog of hedgehog Expressed by the Notochord. Cell 76, 761-775 (Feb. 25, 1994).

Roelink, H. et al. Floor Plate and Motor Neuron Induction by Different Concentrations of the Amino-Terminal Cleavage Product of Sonic Hedgehog Autoproteolysis. Cell 81, 445-455 (1995).

St.-Jaques, B. et al. Sonic hedgehog signaling is essential for hair development. Current Biol. 8, 1058-1068 (1998).

Stone, D.M. et al. The tumour-suppressor gene patched encodes a candidate receptor for Sonic hedgehog. Nature 384, 129-134 (Nov. 14, 1996).

Takabatake, T. et al. Hedgehog and patched gene expression in adult ocular tissues. FEBS Letts. 410, 485-489 (1997).

Therond, P.P. et al. Phosphorylation of the fused protein kinase in response to signaling from hedgehog. PNAS 93, 4224-4228 (1996).

Wang, M.Z. et al. Induction of dopaminergic neuron phenotype in the midbrain by Sonic hedgehog protein. Nature Med. 1, 1184-1188 (1995).

U.S. Appl. No. 10/129,162, filed Mar. 14, 2003, Strauch et al.

\* cited by examiner

Figure 1 : Alignment of N-terminal fragments of Human Hedgehog Proteins

```
        1
Indian  CGPGRVVGSR  RRPPRK-LVP  LAYKQFSPNV  PEKTLGASGR  YEGKIARSSE
Sonic   CGPGRGFG-K  RRHPKK-LTP  LAYKQFIPNV  AEKTLGASGR  YEGKISRNSE
Desert  CGPGRGPVGR  RRYARKQLVP  LLYKQFVPGV  PERTLGASGP  AEGRVARGSE 51
Indian  RFKELTPNYN  PDIIFKDEEN  TGADRLMTQR  CKDRLNSLAI  SVMNQWPGVK
Sonic   RFKELTPNYN  PDIIFKDEEN  TGADRLMTQR  CKDKLNALAI  SVMNQWPGVK
Desert  RFRDLVPNYN  PDIIFKDEEN  SGADRLMTER  CKERVNALAI  AVMNMWPGVR 101
Indian  LRVTEGWDED  GHHSEESLHY  EGRAVDITTS  DRDRNKYGLL  ARLAVEAGFD
Sonic   LRVTEGWDED  GHHSEESLHY  EGRAVDITTS  DRDRSKYGML  ARLAVEAGFD
Desert  LRVTEGWDED  GHHAQDSLHY  EGRALDITTS  DRDRNKYGLL  ARLAVEAGFD 151
Indian  WVYYESKAHV  HCSVKSEHSA  AAKTGG      SEQ ID NO: 1
Sonic   WVYYESKAHI  HCSVKAENSV  AAKSGG      SEQ ID NO: 2
Desert  WVYYESRNHV  HVSVKADNSL  AVRAGG      SEQ ID NO: 3
```

Gap(s), indicated by -, added to facilitate alignment

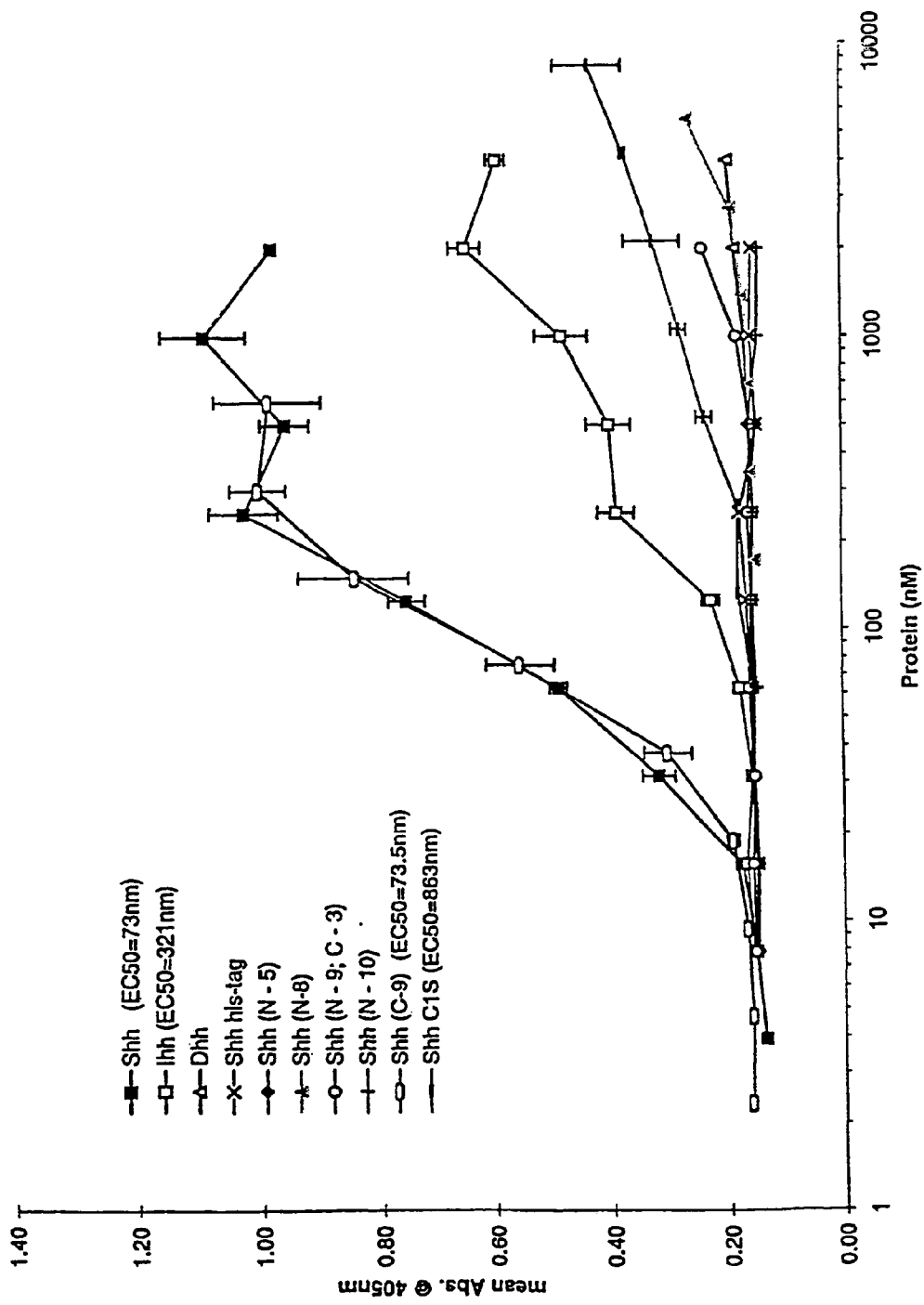

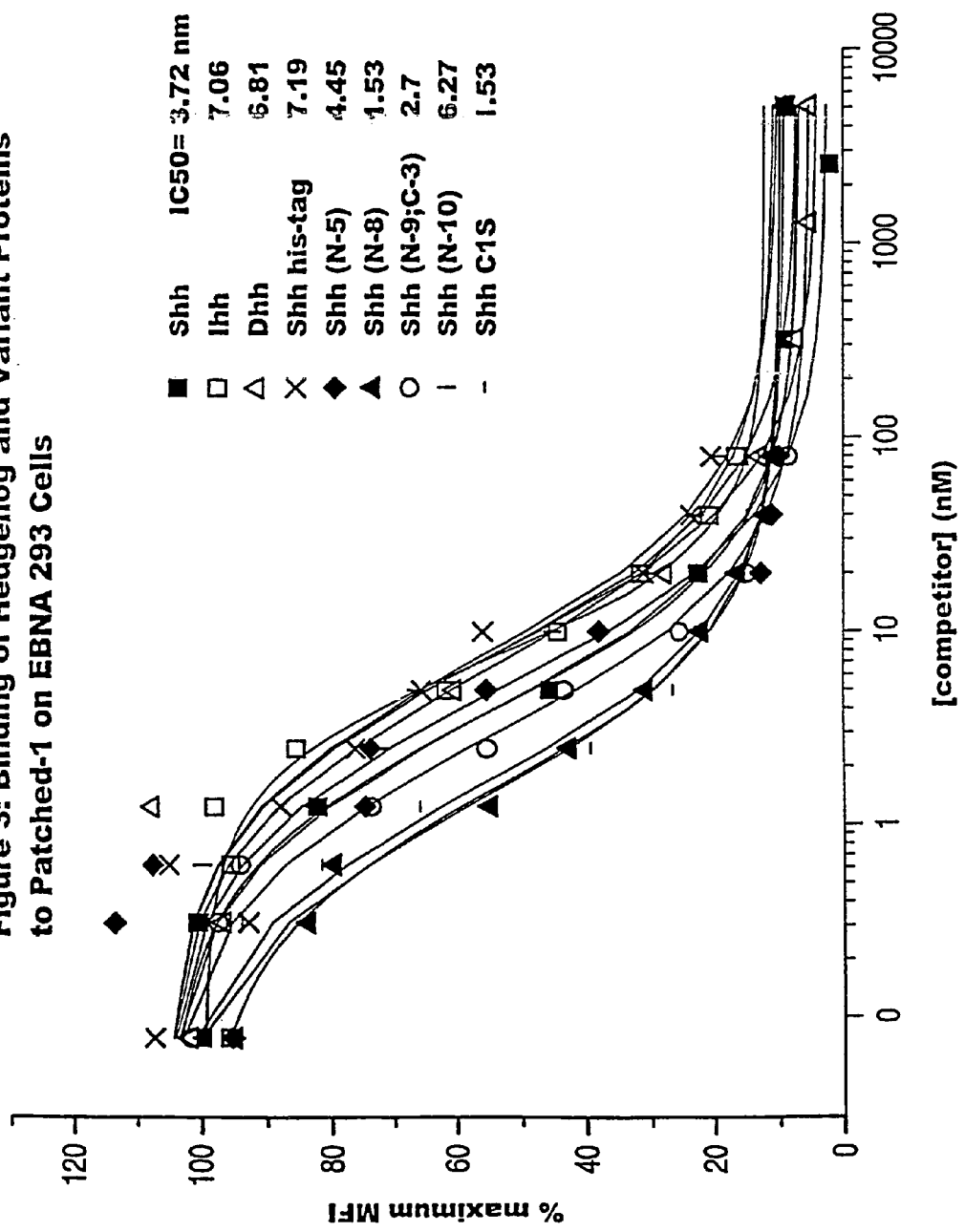

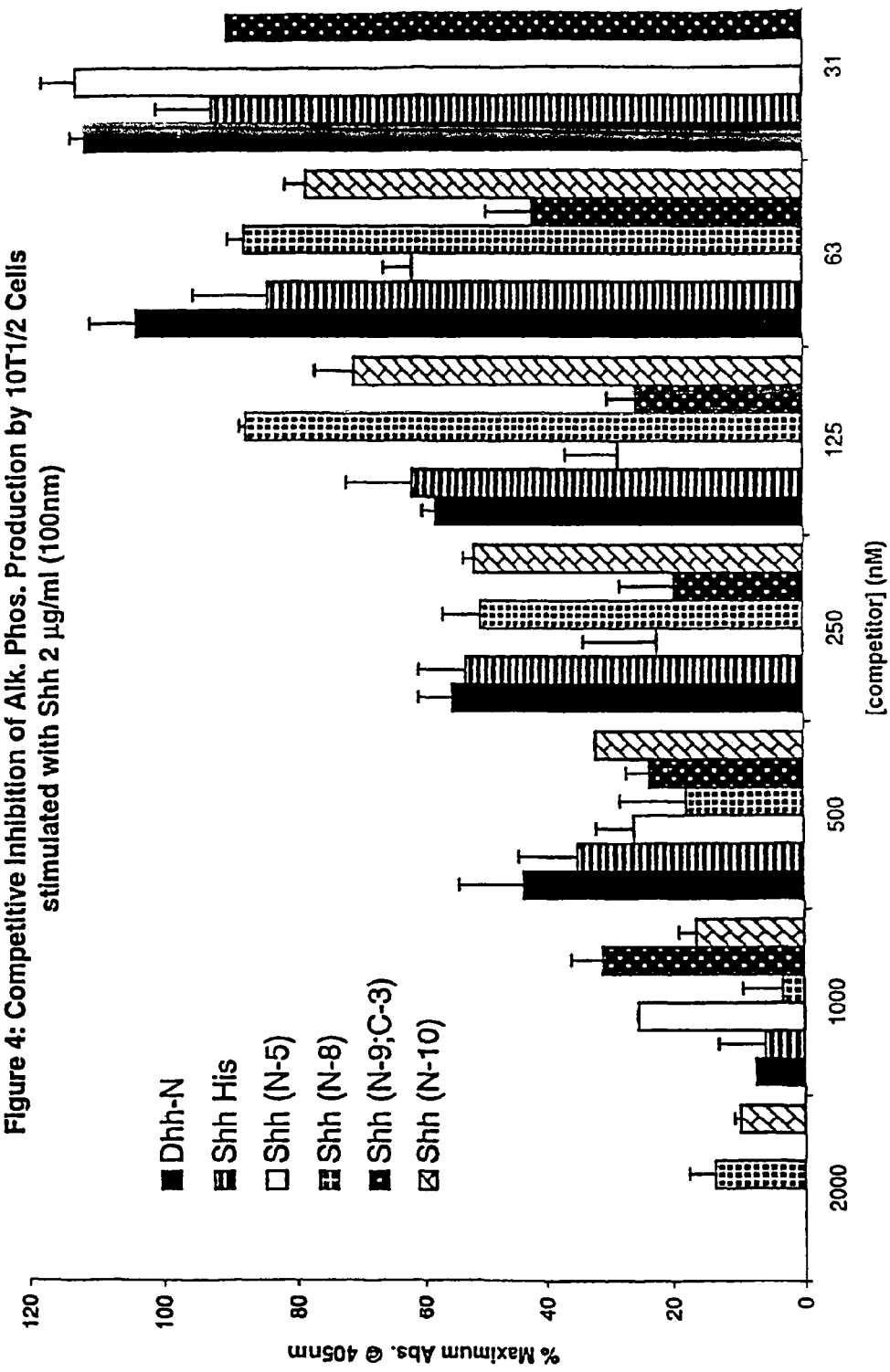

SEQUENCE LISTING

```
<160> NUMBER OF SEQ ID NOS: 19

<210> SEQ ID NO 1
<211> LENGTH: 192
<212> TYPE: PRT
<213> ORGANISM: Homo sapiens

<400> SEQUENCE: 1

Met Gly Ser Ser His His His His His His Ser Ser Gly Asp Asp Asp
 1               5                  10                  15

Asp Lys Cys Gly Pro Gly Arg Gly Phe Gly Lys Arg Arg His Pro Lys
                20                  25                  30

Lys Leu Thr Pro Leu Ala Tyr Lys Gln Phe Ile Pro Asn Val Ala Glu
            35                  40                  45

Lys Thr Leu Gly Ala Ser Gly Arg Tyr Glu Gly Lys Ile Ser Arg Asn
        50                  55                  60

Ser Glu Arg Phe Lys Glu Leu Thr Pro Asn Tyr Asn Pro Asp Ile Ile
65                  70                  75                  80

Phe Lys Asp Glu Glu Asn Thr Gly Ala Asp Arg Leu Met Thr Gln Arg
                85                  90                  95

Cys Lys Asp Lys Leu Asn Ala Leu Ala Ile Ser Val Met Asn Gln Trp
                100                 105                 110

Pro Gly Val Lys Leu Arg Val Thr Glu Gly Trp Asp Glu Asp Gly His
            115                 120                 125

His Ser Glu Glu Ser Leu His Tyr Glu Gly Arg Ala Val Asp Ile Thr
        130                 135                 140

Thr Ser Asp Arg Asp Arg Ser Lys Tyr Gly Met Leu Ala Arg Leu Ala
145                 150                 155                 160

Val Glu Ala Gly Phe Asp Trp Val Tyr Tyr Glu Ser Lys Ala His Ile
                165                 170                 175

His Cys Ser Val Lys Ala Glu Asn Ser Val Ala Ala Lys Ser Gly Gly
                180                 185                 190

<210> SEQ ID NO 2
<211> LENGTH: 175
<212> TYPE: PRT
<213> ORGANISM: Homo sapiens
```

<400> SEQUENCE: 2

Cys Gly Pro Gly Arg Val Gly Ser Arg Arg Pro Pro Arg Lys
1               5                   10                  15

Leu Val Pro Leu Ala Tyr Lys Gln Phe Ser Pro Asn Val Pro Glu Lys
                20                  25                  30

Thr Leu Gly Ala Ser Gly Arg Tyr Glu Gly Lys Ile Ala Arg Ser Ser
            35                  40                  45

Glu Arg Phe Lys Glu Leu Thr Pro Asn Tyr Asn Pro Asp Ile Ile Phe
50                  55                  60

Lys Asp Glu Glu Asn Thr Gly Ala Asp Arg Leu Met Thr Gln Arg Cys
65                  70                  75                  80

Lys Asp Arg Leu Asn Ser Leu Ala Ile Ser Val Met Asn Gln Trp Pro
                85                  90                  95

Gly Val Lys Leu Arg Val Thr Glu Gly Trp Asp Glu Asp Gly His His
            100                 105                 110

Ser Glu Glu Ser Leu His Tyr Glu Gly Arg Ala Val Asp Ile Thr Thr
        115                 120                 125

Ser Asp Arg Asp Arg Asn Lys Tyr Gly Leu Leu Ala Arg Leu Ala Val
130                 135                 140

Glu Ala Gly Phe Asp Trp Val Tyr Tyr Glu Ser Lys Ala His Val His
145                 150                 155                 160

Cys Ser Val Lys Ser Glu His Ser Ala Ala Lys Thr Gly Gly
                165                 170                 175

<210> SEQ ID NO 3
<211> LENGTH: 174
<212> TYPE: PRT
<213> ORGANISM: Homo sapiens

<400> SEQUENCE: 3

Cys Gly Pro Gly Arg Gly Phe Gly Lys Arg Arg His Pro Lys Lys Leu
1               5                   10                  15

Thr Pro Leu Ala Tyr Lys Gln Phe Ile Pro Asn Val Ala Glu Lys Thr
                20                  25                  30

Leu Gly Ala Ser Gly Arg Tyr Glu Gly Lys Ile Ser Arg Asn Ser Glu
            35                  40                  45

Arg Phe Lys Glu Leu Thr Pro Asn Tyr Asn Pro Asp Ile Ile Phe Lys
50                  55                  60

Asp Glu Glu Asn Thr Gly Ala Asp Arg Leu Met Thr Gln Arg Cys Lys
65                  70                  75                  80

Asp Lys Leu Asn Ala Leu Ala Ile Ser Val Met Asn Gln Trp Pro Gly
                85                  90                  95

Val Lys Leu Arg Val Thr Glu Gly Trp Asp Glu Asp Gly His His Ser
            100                 105                 110

Glu Glu Ser Leu His Tyr Glu Gly Arg Ala Val Asp Ile Thr Thr Ser
        115                 120                 125

Asp Arg Asp Arg Ser Lys Tyr Gly Met Leu Ala Arg Leu Ala Val Glu
130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly
                165                 170

<210> SEQ ID NO 4
<211> LENGTH: 176

```
<212> TYPE: PRT
<213> ORGANISM: Homo sapiens

<400> SEQUENCE: 4

Cys Gly Pro Gly Arg Gly Pro Val Gly Arg Arg Tyr Ala Arg Lys
 1               5                  10                  15

Gln Leu Val Pro Leu Leu Tyr Lys Gln Phe Val Pro Gly Val Pro Glu
            20                  25                  30

Arg Thr Leu Gly Ala Ser Gly Pro Ala Glu Gly Arg Val Ala Arg Gly
            35                  40                  45

Ser Glu Arg Phe Arg Asp Leu Val Pro Asn Tyr Asn Pro Asp Ile Ile
    50                  55                  60

Phe Lys Asp Glu Glu Asn Ser Gly Ala Asp Arg Leu Met Thr Glu Arg
65                  70                  75                  80

Cys Lys Glu Arg Val Asn Ala Leu Ala Ile Ala Val Met Asn Met Trp
                85                  90                  95

Pro Gly Val Arg Leu Arg Val Thr Glu Gly Trp Asp Glu Asp Gly His
            100                 105                 110

His Ala Gln Asp Ser Leu His Tyr Glu Gly Arg Ala Leu Asp Ile Thr
        115                 120                 125

Thr Ser Asp Arg Asp Arg Asn Lys Tyr Gly Leu Leu Ala Arg Leu Ala
    130                 135                 140

Val Glu Ala Gly Phe Asp Trp Val Tyr Tyr Glu Ser Arg Asn His Val
145                 150                 155                 160

His Val Ser Val Lys Ala Asp Asn Ser Leu Ala Val Arg Ala Gly Gly
                165                 170                 175

<210> SEQ ID NO 5
<211> LENGTH: 164
<212> TYPE: PRT
<213> ORGANISM: Homo sapiens

<400> SEQUENCE: 5

Arg His Pro Lys Lys Leu Thr Pro Leu Ala Tyr Lys Gln Phe Ile Pro
 1               5                  10                  15

Asn Val Ala Glu Lys Thr Leu Gly Ala Ser Gly Arg Tyr Glu Gly Lys
            20                  25                  30

Ile Ser Arg Asn Ser Glu Arg Phe Lys Glu Leu Thr Pro Asn Tyr Asn
        35                  40                  45

Pro Asp Ile Ile Phe Lys Asp Glu Glu Asn Thr Gly Ala Asp Arg Leu
    50                  55                  60

Met Thr Gln Arg Cys Lys Asp Lys Leu Asn Ala Leu Ala Ile Ser Val
65                  70                  75                  80

Met Asn Gln Trp Pro Gly Val Lys Leu Arg Val Thr Glu Gly Trp Asp
                85                  90                  95

Glu Asp Gly His His Ser Glu Glu Ser Leu His Tyr Glu Gly Arg Ala
            100                 105                 110

Val Asp Ile Thr Thr Ser Asp Arg Asp Arg Ser Lys Tyr Gly Met Leu
        115                 120                 125

Ala Arg Leu Ala Val Glu Ala Gly Phe Asp Trp Val Tyr Tyr Glu Ser
    130                 135                 140

Lys Ala His Ile His Cys Ser Val Lys Ala Glu Asn Ser Val Ala Ala
145                 150                 155                 160

Lys Ser Gly Gly

<210> SEQ ID NO 6
```

<211> LENGTH: 162
<212> TYPE: PRT
<213> ORGANISM: Homo sapiens

<400> SEQUENCE: 6

```
Arg Arg His Pro Lys Lys Leu Thr Pro Leu Ala Tyr Lys Gln Phe Ile
  1               5                  10                  15

Pro Asn Val Ala Glu Lys Thr Leu Gly Ala Ser Gly Arg Tyr Glu Gly
             20                  25                  30

Lys Ile Ser Arg Asn Ser Glu Arg Phe Lys Glu Leu Thr Pro Asn Tyr
         35                  40                  45

Asn Pro Asp Ile Ile Phe Lys Asp Glu Glu Asn Thr Gly Ala Asp Arg
 50                  55                  60

Leu Met Thr Gln Arg Cys Lys Asp Lys Leu Asn Ala Leu Ala Ile Ser
 65                  70                  75                  80

Val Met Asn Gln Trp Pro Gly Val Lys Leu Arg Val Thr Glu Gly Trp
                 85                  90                  95

Asp Glu Asp Gly His His Ser Glu Glu Ser Leu His Tyr Glu Gly Arg
            100                 105                 110

Ala Val Asp Ile Thr Thr Ser Asp Arg Asp Arg Ser Lys Tyr Gly Met
        115                 120                 125

Leu Ala Arg Leu Ala Val Glu Ala Gly Phe Asp Trp Val Tyr Tyr Glu
130                 135                 140

Ser Lys Ala His Ile His Cys Ser Val Lys Ala Glu Asn Ser Val Ala
145                 150                 155                 160

Ala Lys
```

<210> SEQ ID NO 7
<211> LENGTH: 169
<212> TYPE: PRT
<213> ORGANISM: Homo sapiens

<400> SEQUENCE: 7

```
Gly Phe Gly Lys Arg Arg His Pro Lys Lys Leu Thr Pro Leu Ala Tyr
  1               5                  10                  15

Lys Gln Phe Ile Pro Asn Val Ala Glu Lys Thr Leu Gly Ala Ser Gly
             20                  25                  30

Arg Tyr Glu Gly Lys Ile Ser Arg Asn Ser Glu Arg Phe Lys Glu Leu
         35                  40                  45

Thr Pro Asn Tyr Asn Pro Asp Ile Ile Phe Lys Asp Glu Glu Asn Thr
 50                  55                  60

Gly Ala Asp Arg Leu Met Thr Gln Arg Cys Lys Asp Lys Leu Asn Ala
 65                  70                  75                  80

Leu Ala Ile Ser Val Met Asn Gln Trp Pro Gly Val Lys Leu Arg Val
                 85                  90                  95

Thr Glu Gly Trp Asp Glu Asp Gly His His Ser Glu Glu Ser Leu His
            100                 105                 110

Tyr Glu Gly Arg Ala Val Asp Ile Thr Thr Ser Asp Arg Asp Arg Ser
        115                 120                 125

Lys Tyr Gly Met Leu Ala Arg Leu Ala Val Glu Ala Gly Phe Asp Trp
130                 135                 140

Val Tyr Tyr Glu Ser Lys Ala His Ile His Cys Ser Val Lys Ala Glu
145                 150                 155                 160

Asn Ser Val Ala Ala Lys Ser Gly Gly
                165
```

```
<210> SEQ ID NO 8
<211> LENGTH: 174
<212> TYPE: PRT
<213> ORGANISM: Homo sapiens

<400> SEQUENCE: 8

Ser Gly Pro Gly Arg Gly Phe Gly Lys Arg Arg His Pro Lys Lys Leu
  1               5                  10                  15

Thr Pro Leu Ala Tyr Lys Gln Phe Ile Pro Asn Val Ala Glu Lys Thr
             20                  25                  30

Leu Gly Ala Ser Gly Arg Tyr Glu Gly Lys Ile Ser Arg Asn Ser Glu
         35                  40                  45

Arg Phe Lys Glu Leu Thr Pro Asn Tyr Asn Pro Asp Ile Ile Phe Lys
     50                  55                  60

Asp Glu Glu Asn Thr Gly Ala Asp Arg Leu Met Thr Gln Arg Cys Lys
 65                  70                  75                  80

Asp Lys Leu Asn Ala Leu Ala Ile Ser Val Met Asn Gln Trp Pro Gly
                 85                  90                  95

Val Lys Leu Arg Val Thr Glu Gly Trp Asp Glu Asp Gly His His Ser
            100                 105                 110

Glu Glu Ser Leu His Tyr Glu Gly Arg Ala Val Asp Ile Thr Thr Ser
        115                 120                 125

Asp Arg Asp Arg Ser Lys Tyr Gly Met Leu Ala Arg Leu Ala Val Glu
    130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly
                165                 170

<210> SEQ ID NO 9
<211> LENGTH: 166
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (3)..(3)
<223> OTHER INFORMATION: Xaa=Phe, His or Tyr
<220> FEATURE:
<221> NAME/KEY: MISC_FEATURE
<222> LOCATION: (4)..(4)
<223> OTHER INFORMATION: Xaa=Phe or Ala
<220> FEATURE:
<221> NAME/KEY: MISC_FEATURE
<222> LOCATION: (5)..(5)
<223> OTHER INFORMATION: Xaa=Arg or Lys
<220> FEATURE:
<221> NAME/KEY: MISC_FEATURE
<222> LOCATION: (7)..(7)
<223> OTHER INFORMATION: Xaa=any amino acid
<220> FEATURE:
<221> NAME/KEY: MISC_FEATURE
<222> LOCATION: (9)..(9)
<223> OTHER INFORMATION: Xaa=Val or Thr
<220> FEATURE:
<221> NAME/KEY: MISC_FEATURE
<222> LOCATION: (12)..(12)
<223> OTHER INFORMATION: Xaa=Ala or Leu
<220> FEATURE:
<221> NAME/KEY: MISC_FEATURE
<222> LOCATION: (17)..(17)
<223> OTHER INFORMATION: Xaa=Ser, Ile or Val
<220> FEATURE:
<221> NAME/KEY: MISC_FEATURE
<222> LOCATION: (19)..(19)
<223> OTHER INFORMATION: Xaa=Asn or Gly
<220> FEATURE:
```

```
<221> NAME/KEY: MISC_FEATURE
<222> LOCATION: (21)..(21)
<223> OTHER INFORMATION: Xaa=Pro or Ala
<220> FEATURE:
<221> NAME/KEY: MISC_FEATURE
<222> LOCATION: (31)..(31)
<223> OTHER INFORMATION: Xaa=Tyr or Ala
<220> FEATURE:
<221> NAME/KEY: MISC_FEATURE
<222> LOCATION: (35)..(35)
<223> OTHER INFORMATION: Xaa=Ile or Val
<220> FEATURE:
<221> NAME/KEY: MISC_FEATURE
<222> LOCATION: (36)..(36)
<223> OTHER INFORMATION: Xaa=Ala or Ser
<220> FEATURE:
<221> NAME/KEY: MISC_FEATURE
<222> LOCATION: (38)..(38)
<223> OTHER INFORMATION: Xaa=Ser, Asn or Gly
<220> FEATURE:
<221> NAME/KEY: MISC_FEATURE
<222> LOCATION: (44)..(44)
<223> OTHER INFORMATION: Xaa=Glu or Asp
<220> FEATURE:
<221> NAME/KEY: MISC_FEATURE
<222> LOCATION: (46)..(46)
<223> OTHER INFORMATION: Xaa=Thr or Val
<220> FEATURE:
<221> NAME/KEY: MISC_FEATURE
<222> LOCATION: (61)..(61)
<223> OTHER INFORMATION: Xaa=Thr or Ser
<220> FEATURE:
<221> NAME/KEY: MISC_FEATURE
<222> LOCATION: (69)..(69)
<223> OTHER INFORMATION: Xaa=Gln or Glu
<220> FEATURE:
<221> NAME/KEY: MISC_FEATURE
<222> LOCATION: (73)..(73)
<223> OTHER INFORMATION: Xaa=Asp or Glu
<220> FEATURE:
<221> NAME/KEY: MISC_FEATURE
<222> LOCATION: (75)..(75)
<223> OTHER INFORMATION: Xaa=Leu or Val
<220> FEATURE:
<221> NAME/KEY: MISC_FEATURE
<222> LOCATION: (74)..(74)
<223> OTHER INFORMATION: Xaa=Arg or Lys
<220> FEATURE:
<221> NAME/KEY: MISC_FEATURE
<222> LOCATION: (81)..(81)
<223> OTHER INFORMATION: Xaa=Leu or Val
<220> FEATURE:
<221> NAME/KEY: MISC_FEATURE
<222> LOCATION: (85)..(85)
<223> OTHER INFORMATION: Xaa=Ser or Ala
<220> FEATURE:
<221> NAME/KEY: MISC_FEATURE
<222> LOCATION: (104)..(104)
<223> OTHER INFORMATION: Xaa=Gln or Met
<220> FEATURE:
<221> NAME/KEY: MISC_FEATURE
<222> LOCATION: (105)..(105)
<223> OTHER INFORMATION: Xaa=Ser or Ala
<220> FEATURE:
<221> NAME/KEY: MISC_FEATURE
<222> LOCATION: (106)..(106)
<223> OTHER INFORMATION: Xaa=Glu or Gln
<220> FEATURE:
<221> NAME/KEY: MISC_FEATURE
<222> LOCATION: (125)..(125)
<223> OTHER INFORMATION: Xaa=Glu or Asp
<220> FEATURE:
<221> NAME/KEY: MISC_FEATURE
<222> LOCATION: (129)..(129)
<223> OTHER INFORMATION: Xaa=Asn or Ser
<220> FEATURE:
<221> NAME/KEY: MISC_FEATURE
<222> LOCATION: (147)..(147)
<223> OTHER INFORMATION: Xaa=Leu or Met
<220> FEATURE:
```

```
<221> NAME/KEY: MISC_FEATURE
<222> LOCATION: (148)..(148)
<223> OTHER INFORMATION: Xaa=Lys or Arg
<220> FEATURE:
<221> NAME/KEY: MISC_FEATURE
<222> LOCATION: (152)..(152)
<223> OTHER INFORMATION: Xaa=Ala or Asn
<220> FEATURE:
<221> NAME/KEY: MISC_FEATURE
<222> LOCATION: (156)..(156)
<223> OTHER INFORMATION: Xaa=Val or Ile
<220> FEATURE:
<221> NAME/KEY: MISC_FEATURE
<222> LOCATION: (150)..(150)
<223> OTHER INFORMATION: Xaa=Val or Ile
<220> FEATURE:
<221> NAME/KEY: MISC_FEATURE
<222> LOCATION: (157)..(157)
<223> OTHER INFORMATION: Xaa=Ser or Ala
<220> FEATURE:
<221> NAME/KEY: MISC_FEATURE
<222> LOCATION: (158)..(158)
<223> OTHER INFORMATION: Xaa=Glu or Asp
<220> FEATURE:
<221> NAME/KEY: MISC_FEATURE
<222> LOCATION: (160)..(160)
<223> OTHER INFORMATION: Xaa=His or Asn
<220> FEATURE:
<221> NAME/KEY: MISC_FEATURE
<222> LOCATION: (163)..(163)
<223> OTHER INFORMATION: Xaa=Lys or Arg
<220> FEATURE:
<221> NAME/KEY: MISC_FEATURE
<222> LOCATION: (164)..(164)
<223> OTHER INFORMATION: Xaa=Thr, Ser or Ala

<400> SEQUENCE: 9

Arg Arg Xaa Xaa Xaa Lys Xaa Leu Xaa Pro Leu Xaa Tyr Lys Gln Phe
1               5                   10                  15

Xaa Pro Xaa Val Xaa Glu Lys Thr Leu Gly Ala Ser Gly Arg Xaa Glu
            20                  25                  30

Gly Lys Xaa Xaa Arg Xaa Ser Glu Arg Phe Lys Xaa Leu Xaa Pro Asn
        35                  40                  45

Tyr Asn Pro Asp Ile Ile Phe Lys Asp Glu Glu Asn Xaa Gly Ala Asp
50                  55                  60

Arg Leu Met Thr Xaa Arg Cys Lys Xaa Xaa Xaa Asn Ser Leu Ala Ile
65                  70                  75                  80

Xaa Val Met Asn Xaa Trp Pro Gly Val Lys Leu Arg Val Thr Glu Gly
                85                  90                  95

Trp Asp Glu Asp Gly His His Xaa Xaa Xaa Ser Leu His Tyr Glu Gly
            100                 105                 110

Arg Ala Val Asp Ile Thr Thr Ser Asp Arg Asp Arg Xaa Lys Tyr Gly
        115                 120                 125

Xaa Leu Ala Arg Leu Ala Val Glu Ala Gly Phe Asp Trp Val Tyr Tyr
130                 135                 140

Glu Ser Xaa Xaa His Xaa His Xaa Ser Val Lys Xaa Xaa Xaa Ser Xaa
145                 150                 155                 160

Ala Ala Xaa Xaa Gly Gly
            165

<210> SEQ ID NO 10
<211> LENGTH: 165
<212> TYPE: PRT
<213> ORGANISM: Homo sapiens

<400> SEQUENCE: 10

Cys Gly Pro Gly Arg Gly Phe Gly Lys Arg Arg His Pro Lys Lys Leu
```

```
                1               5                  10                 15
           Thr Pro Leu Ala Tyr Lys Gln Phe Ile Pro Asn Val Ala Glu Lys Thr
                            20                  25                  30

Leu Gly Ala Ser Gly Arg Tyr Glu Gly Lys Ile Ser Arg Asn Ser Glu
                            35                  40                  45

Arg Phe Lys Glu Leu Thr Pro Asn Tyr Asn Pro Asp Ile Ile Phe Lys
            50                  55                  60

Asp Glu Glu Asn Thr Gly Ala Asp Arg Leu Met Thr Gln Arg Cys Lys
            65                  70                  75                  80

Asp Lys Leu Asn Ala Leu Ala Ile Ser Val Met Asn Gln Trp Pro Gly
                            85                  90                  95

Val Lys Leu Arg Val Thr Glu Gly Trp Asp Glu Asp Gly His His Ser
                            100                 105                 110

Glu Glu Ser Leu His Tyr Glu Gly Arg Ala Val Asp Ile Thr Thr Ser
                            115                 120                 125

Asp Arg Asp Arg Ser Lys Tyr Gly Met Leu Ala Arg Leu Ala Val Glu
            130                 135                 140

Ala Gly Phe Asp Trp Val Tyr Tyr Glu Ser Lys Ala His Ile His Cys
            145                 150                 155                 160

Ser Val Lys Ala Glu
                            165

<210> SEQ ID NO 11
<211> LENGTH: 166
<212> TYPE: PRT
<213> ORGANISM: Homo sapiens

<400> SEQUENCE: 11

Lys Arg Arg His Pro Lys Lys Leu Thr Pro Leu Ala Tyr Lys Gln Phe
            1               5                   10                  15

Ile Pro Asn Val Ala Glu Lys Thr Leu Gly Ala Ser Gly Arg Tyr Glu
                            20                  25                  30

Gly Lys Ile Ser Arg Asn Ser Glu Arg Phe Lys Glu Leu Thr Pro Asn
                            35                  40                  45

Tyr Asn Pro Asp Ile Ile Phe Lys Asp Glu Glu Asn Thr Gly Ala Asp
                            50                  55                  60

Arg Leu Met Thr Gln Arg Cys Lys Asp Lys Leu Asn Ala Leu Ala Ile
            65                  70                  75                  80

Ser Val Met Asn Gln Trp Pro Gly Val Lys Leu Arg Val Thr Glu Gly
                            85                  90                  95

Trp Asp Glu Asp Gly His His Ser Glu Glu Ser Leu His Tyr Glu Gly
                            100                 105                 110

Arg Ala Val Asp Ile Thr Thr Ser Asp Arg Asp Arg Ser Lys Tyr Gly
                            115                 120                 125

Met Leu Ala Arg Leu Ala Val Glu Ala Gly Phe Asp Trp Val Tyr Tyr
            130                 135                 140

Glu Ser Lys Ala His Ile His Cys Ser Val Lys Ala Glu Asn Ser Val
            145                 150                 155                 160

Ala Ala Lys Ser Gly Gly
                            165

<210> SEQ ID NO 12
<211> LENGTH: 25
<212> TYPE: DNA
<213> ORGANISM: Homo sapiens

<400> SEQUENCE: 12
```

```
cattggcagg aggagttgat tgtgg                                         25

<210> SEQ ID NO 13
<211> LENGTH: 25
<212> TYPE: DNA
<213> ORGANISM: Homo sapiens

<400> SEQUENCE: 13 agcaccttt gagtggagtt tgggg                                          25

<210> SEQ ID NO 14
<211> LENGTH: 23
<212> TYPE: DNA
<213> ORGANISM: Homo sapiens

<400> SEQUENCE: 14
cggggtctca aactgcccag ctt                                           23

<210> SEQ ID NO 15
<211> LENGTH: 19
<212> TYPE: DNA
<213> ORGANISM: Homo sapiens

<400> SEQUENCE: 15
ggctgggtca ctggccctc                                                19

<210> SEQ ID NO 16
<211> LENGTH: 492
<212> TYPE: DNA
<213> ORGANISM: Homo sapiens

<400> SEQUENCE: 16
aggcacccca aaaagctgac cccttagcc tacaagcagt ttatccccaa tgtggccgag    60
aagaccctag gcgccagcgg aaggtatgaa gggaagatct ccagaaactc cgagcgattt  120
aaggaactca ccccccaatta caaccccgac atcatattta aggatgaaga aaacaccgga  180
gcggacaggc tgatgactca gaggtgtaag gacaagttga acgctttggc catctcggtg  240
atgaaccagt ggccaggagt gaaactgcgg gtgaccgagg gctgggacga agatggccac  300
cactcagagg agtctctgca ctacgagggc cgcgcagtgg acatcaccac gtctgaccgc  360
gaccgcagca agtacggcat gctggcccgc ctggcggtgg aggccggctt cgactgggtg  420
tactacgagt ccaaggcaca tatccactgc tcggtgaaag cagagaactc ggtggcggcc  480
aaatcgggag gc                                                      492

<210> SEQ ID NO 17
<211> LENGTH: 522
<212> TYPE: DNA
<213> ORGANISM: Homo sapiens

<400> SEQUENCE: 17
tcgggcccgg gcaggggtt cgggaagagg aggcacccca aaaagctgac cccttagcc    60 tacaagcagt ttatccccaa tgtggccgag aagaccctag gcgccagcgg aaggtatgaa  120
gggaagatct ccagaaactc cgagcgattt aaggaactca ccccccaatta caaccccgac  180 atcatattta aggatgaaga aaacaccgga gcggacaggc tgatgactca gaggtgtaag  240
gacaagttga acgctttggc catctcggtg atgaaccagt ggccaggagt gaaactgcgg  300
gtgaccgagg gctgggacga agatggccac cactcagagg agtctctgca ctacgagggc  360
cgcgcagtgg acatcaccac gtctgaccgc gaccgcagca agtacggcat gctggcccgc  420
```

```
ctggcggtgg aggccggctt cgactgggtg tactacgagt ccaaggcaca tatccactgc    480
tcggtgaaag cagagaactc ggtggcggcc aaatcgggag gc                       522

<210> SEQ ID NO 18
<211> LENGTH: 30
<212> TYPE: DNA
<213> ORGANISM: Homo sapiens

<400> SEQUENCE: 18
tcgagaaaag atgcggaccg ggcagggggt                                      30

<210> SEQ ID NO 19
<211> LENGTH: 29
<212> TYPE: DNA
<213> ORGANISM: Homo sapiens

<400> SEQUENCE: 19
cgaaccccct gcccggtccg catcttttc                                       29
```

FUNCTIONAL ANTAGONISTS OF HEDGEHOG ACTIVITY

CROSS-REFERENCE TO RELATED APPLICATIONS

This application is a continuation of U.S. application Ser. No. 09/890,975, international filing date Nov. 2, 1999 now abandoned, which is a national stage filing under 35 U.S.C. 371 of PCT application PCT/US99/25700, filed Nov. 2, 1999, which claims priority from U.S. Provisional Application No. 60/106,703, filed Nov. 2, 1998, the specifications of all of which are incorporated by reference herein. PCT Application PCT/US99/25700 was published under PCT Article 21(2) in English.

BACKGROUND OF THE INVENTION

The hedgehog proteins are a family of extracellular signaling proteins that regulate various aspects of embryonic development both in vertebrates and in invertebrates (for reviews see Perrimon, N. (1995) Cell 80, 517-520 and Johnson, R. L., and Tabin, C. (1995) Cell 81, 313-316). The family includes members obtained from a variety of animals and includes Sonic, Desert, and Indian hedgehog. The most extensively characterized mammalian homolog is Sonic hedgehog ("Shh"), which is involved in diverse embryonic induction events, including the induction of floor plate and the establishment of ventral polarity within the central nervous system as well as proper anterior-posterior patterning of the developing limb (See Riddle, R. D., et al. (1993) Cell 75, 1401-1416; Echelard, Y. et al. (1993) Cell 75, 1417-1471; Roelink, H., et al. (1994) Cell 76, 761-775; and Roelink, H., et al. (1995) Cell 81, 445-455). In mediating these effects, Shh is believed to act both as a short range, contact-dependent inducer and as a long range, diffusible morphogen. Shh is expressed in the embryonic notochord, and induces floor plate formation at the ventral midline of the neural tube in a contact-dependent manner (See Riddle et al., and Roelink et al., Cell, 81:445 supra). Data suggest Shh can also act as a long range, diffusible morphogen, to promote subsequent differentiation of ventral neurons in a region-specific manner; e.g., dopaminergic neurons in the midbrain (Wang, M. Z. et al., (1995), Nature Med. 1, 1184-1188), and motor neurons in the spinal cord (Roelink et al, Cell 81: 445, supra).

Biochemical and genetic data suggest that the hedgehog receptor is the product of the tumor suppressor gene patched (Marigo, V., et al. (1996) Nature 384, 176179; Stone, D. M., et al. (1996) Nature 384, 129-134) and that other proteins, including smoothened (Alcedo, J., et al. (1996) Cell 86, 221-232), Cubitus interruptus or its mammalian counterpart gli (Dominguez, M., et al. (1996) Science 272, 1621-1625; Alexandre, C., et al. (1996) Genes & Dev. 10, 2003-2013), and fused (Therond, P. P., et al. (1996) Proc. Natl. Acad. Sci. USA 93, 4224-4228), are involved in the hedgehog signaling pathway. Induction of patched-1 and gli-1 expression are downstream markers of hedgehog signaling and serve as simple markers for hedgehog function. A second patched gene, patched-2 is also induced by hedgehog (Takabatake, T., et al., (1997) FEBS Letts. 410, 485-489). Hip, a transmembrane protein, has also been identified as a receptor for Hedgehog (PCT Publication WO98/12326).

Shh is synthesized as a 45 kDa precursor protein that is cleaved autocatalytically to yield a 20 kDa N-terminal fragment that is responsible for all known hedgehog biological activity ("mature" Sonic hedgehog) and a 25 kDa C-terminal fragment that contains the autoprocessing machinery (Lee, J., et al. (1994) Science 266, 1528-1536; Bumcrot, D. A., et al. (1995) Mol. Cell Biol. 15, 2294-2303; Porter, J. A., et al. (1995) Nature 374, 363-366). The N-terminal fragment remains membrane-associated through the addition of a lipid tether at its C-terminus (Porter, J. A., et al. (1996) Science 274, 255-258; Porter, J. A., et al. (1995) Cell 86, 21-34). Recent biochemical data have identified this lipid tether as a cholesterol (Porter et al., Science 274, supra), the addition of which is catalyzed by the C-terminal domain during the autoprocessing step. Shh is also modified at its N-terminus with a palmitic acid (as described in PCT patent application Serial Number PCT US98/15923 and in Pepinsky et al., (1998) J. Biol. Chem., 273: 14037-14045). Lipid tethers restrict the tissue localization of the hedgehog signal and have presumably evolved as part of the mechanism for regulating short range-long range signaling by hedgehog.

Certain pathological conditions are caused by overexpression of hedgehog protein, including a variety of neural carcinomas. For these conditions, and others, it would be useful to develop versions of hedgehog that are capable of binding to hedgehog receptor proteins, but do not elicit signaling by hedgehog and, thus, serve as antagonists to hedgehog activity.

SUMMARY OF THE INVENTION

We have discovered that the N-terminal cysteine of mature hedgehog proteins is important for biological activity and that certain hedgehog variants that contain N-terminal alterations can block hedgehog function; thus allowing these variants to serve as functional antagonists. These polypeptides have the ability to bind to the hedgehog receptor, patched-1, but lack, or have reduced ability to, elicit hedgehog-dependent responses.

One aspect of the invention is an isolated, functional antagonist of a hedgehog polypeptide. The critical feature of the primary amino acid sequence that determines whether such a hedgehog polypeptide is a functional hedgehog antagonist is that the hedgehog polypeptide either: (i) lacks the N-terminal cysteine corresponding to Cys-1 of a mature hedgehog or (ii) contains an N-terminal cysteine corresponding to Cys-1 of a mature hedgehog in an altered form. In both cases, the structure of the antagonist is sufficiently similar to that of wild type hedgehog to allow the protein to bind to hedgehog receptor, but not allow induction of a hedgehog-dependent signaling response in C3H10T1/2 cells. The hedgehog polypeptide may be a modified form of any member of the hedgehog family, so long as it contains the critical primary amino acid sequence.

Thus, in one embodiment, the functional antagonist includes an N-terminal extension moiety. This moiety may include the N-terminal cysteine that corresponds to Cys-1 of a mature hedgehog polypeptide. In this embodiment, the N-terminal extension moiety effectively prevents the N-terminal cysteine corresponding to Cys-1 of the mature hedgehog polypeptide from exhibiting biological activity. The N-terminal extension moiety may also replace the Cys-1 of the mature hedgehog polypeptide.

In another embodiment, the functional antagonist is missing no greater than about 12 amino acids beginning from that N-terminal cysteine corresponding to Cys-1 of the mature hedgehog polypeptide.

In yet another embodiment, the functional antagonist has a mutation of the N-terminal cysteine corresponding to Cys-1 of the mature hedgehog polypeptide to a polar or charged amino acid residue, such as serine or aspartic acid.

Another aspect of the invention is an isolated functional antagonist of a hedgehog polypeptide, comprising a hedgehog polypeptide containing an N-terminal cysteine in a modified form, wherein the N-terminal cysteine corresponds to Cys-1 of a mature hedgehog polypeptide but no longer has the activity of the Cys-1 of the mature peptide. In one embodiment, the functional antagonist has an N-terminal cysteine in an oxidized form.

The Cys-1 of the mature hedgehog polypeptide can be selected from the group consisting of (a) Cys-1 of mature Sonic hedgehog polypeptide; (b) Cys-1 of mature Indian hedgehog polypeptide; and (c) Cys-1 of mature Desert hedgehog polypeptide. Preferred isolated, functional antagonists of a hedgehog polypeptide are selected from the group of polypeptides consisting of SEQ ID NOS: 5, 6, 7, 8, and 9.

A further aspect of the invention is an isolated, functional antagonist of a hedgehog polypeptide having at least the following properties: (i) the isolated protein binds the receptor patched-1 with an affinity that may be less than, but is preferably similar to that for the binding of mature hedgehog protein to patched-1; and (ii) the isolated protein blocks alkaline phosphatase (AP) induction by mature hedgehog protein when tested in an in vitro C3H10T1/2 cell-based AP induction assay. The antagonist having these properties may comprise a hedgehog polypeptide lacking the N-terminal cysteine that corresponds to Cys-1 of mature Sonic, Indian or Desert hedgehog.

In preferred embodiments, the antagonist polypeptide includes an amino acid sequence at least 60% homologous to an amino acid sequence from SEQ ID NOS: 1-8 and the antagonist polypeptide is at least 100 amino acids in length. Preferably, the antagonist polypeptide exhibits a functional antagonist biological activity, e.g.,: (i) the isolated protein binds the receptor patched-1 with an affinity that may be less than, but is preferably similar to that for the binding of mature hedgehog protein to patched-1; and (ii) the isolated protein blocks the induction of AP by mature protein when tested in the C3H 10T1/2 cell-based AP induction assay.

Isolated polynucleotides (e.g., RNA or DNA) are also encompassed within the claims. One embodiment of the invention is an isolated DNA sequence encoding, upon expression, a functional antagonist that contains the critical primary amino acid sequence comprising a hedgehog polypeptide lacking that N-terminal cysteine corresponding to Cys-1 of a mature Sonic hedgehog.

In one embodiment, the isolated DNA sequence encodes a functional antagonist that includes an N-terminal extension moiety that contains the Cys-1 of mature Sonic hedgehog. In another embodiment, the isolated DNA sequence encodes a functional antagonist that includes an N-terminal extension moiety that replaces the Cys-1 of mature Sonic hedgehog as the most N-terminal amino acid residue.

In another embodiment, the isolated DNA sequence encodes a functional antagonist that is missing no greater than about 12 amino acids beginning from that N-terminal cysteine corresponding to Cys-1 of mature Sonic hedgehog.

In yet another embodiment, the isolated DNA sequence encodes a functional antagonist that has a mutation of the N-terminal cysteine to another amino acid residue.

Isolated polynucleotides (e.g., RNA or DNA) encoding, upon expression, a functional antagonist that contains the critical primary amino acid sequence comprising a hedgehog polypeptide lacking that N-terminal cysteine corresponding to Cys-1 of a mature Desert or Indian hedgehog are also encompassed within the claims. For example, the isolated DNA sequence of the invention may encode a functional antagonist that includes an N-terminal extension moiety that contains the Cys-1 of mature Desert or Indian. In another embodiment, the isolated DNA sequence encodes a functional antagonist that includes an N-terminal extension moiety that replaces the Cys-1 of mature Desert or Indian hedgehog as the most N-terminal amino acid residue. In another embodiment, the isolated DNA sequence encodes a functional antagonist that is missing no greater than about 12 amino acids beginning from that N-terminal cysteine corresponding to Cys-1 of mature Desert or Indian hedgehog.

In other embodiments, the antagonist polypeptide includes a hedgehog antagonist sequence described herein as well as other N-terminal and/or C-terminal amino acid sequences. The antagonist polypeptide may also include all or a fragment of an amino acid sequence from SEQ ID NOS: 1-4 and 5-8, fused, in reading frame, to additional amino acid residues, preferably to residues encoded by genomic DNA 5' to the genomic DNA which encodes a sequence from SEQ ID NOS: 1-4 and 5-8. In yet other preferred embodiments, the antagonist polypeptide is a protein having a first polypeptide portion and a hedgehog antagonist portion fused or otherwise linked either 5' or 3' to the first polypeptide portion, e.g., the first, additional-polypeptide portion having an amino acid sequence unrelated to an antagonist polypeptide. That is, the additional polypeptide portion can be, e.g., any of glutathione-S-transferase, a DNA binding domain, or a polymerase activating domain, a histidine tag, an immunoglobulin or portion thereof, fused or otherwise linked to either the N- or C-terminus of the antagonist portion. Polypeptides of the invention include those which arise as a result of the existence of multiple genes, alternative transcription events, alternative RNA splicing events, and alternative translational and non-translational events. The polypeptide can be expressed in systems, e.g., cultured cells, which result in substantially the same postranslational modifications present when expressed hedgehog antagonist is expressed in a native cell, or in systems which result in the omission of postranslational modifications present when expressed in a native cell.

Another aspect of the invention is an isolated DNA sequence encoding a functional antagonist comprising a hedgehog polypeptide containing an N-terminal cysteine in a modified form, wherein the N-terminal cysteine corresponds to Cys-1 of a mature Sonic hedgehog. In one embodiment, the DNA sequence encodes a functional antagonist that has an N-terminal cysteine included as part of an N-terminal extension moiety.

Preferred DNA sequences encode hedgehog polypeptides that are selected from the group of polypeptides consisting of SEQ ID NOS: 1-4 and 5-8.

A further aspect of the invention is an isolated DNA sequence encoding a functional antagonist of a hedgehog polypeptide having at least the following properties: (i) the isolated protein binds the receptor patched-1 with an affinity that may be less than, but is at least similar to the binding affinity of mature hedgehog protein to patched-1; and (ii) the isolated protein blocks AP induction by mature hedgehog protein when tested in an in vitro C3H10T1/2 cell-based AP induction assay. The DNA sequence encoding an antagonist having these properties most preferably encodes a hedgehog polypeptide lacking that N-terminal cysteine corresponding to Cys-1 of mature Sonic hedgehog. It is preferred that the DNA sequences of the invention encode a hedgehog polypeptide that is a member of the vertebrate hedgehog family such as those DNA sequences encoding vertebrate hedgehog polypeptides selected from the group consisting of Sonic hedgehog, Indian hedgehog and Desert hedgehog.

Preferred DNA sequences encoding a functional antagonist of a hedgehog polypeptide include a polynucleotide selected from the group consisting of:
(a) SEQ ID NOS.: 16 and 17;
(b) a polynucleotide that hybridizes to any of the foregoing sequences under standard hybridization conditions and that encodes a protein having the activity of a functional antagonist of a hedgehog polypeptide; and
(c) a polynucleotide that codes on expression for a protein encoded by any of the foregoing polynucleotide sequences.

In yet a further preferred embodiment, the polynucleotide which encodes an antagonist polypeptide of the invention, hybridizes under standard conditions to a polynucleotide probe corresponding to at least 12 consecutive nucleotides from SEQ ID NOS: 16 and 17. Another embodiment of the invention includes a DNA sequence that encodes a hedgehog polypeptide that is at least 60% homologous to a polypeptide of the group selected from polypeptide SEQ ID NOS: 1-4 and 5-8.

The subject antagonist polynucleotide may include a transcriptional regulatory sequence, e.g. at least one of a transcriptional promoter or transcriptional enhancer sequence, operatively linked to the hedgehog antagonist gene sequence, e.g., to render the hedgehog antagonist gene sequence suitable for use as an expression vector.

Thus, another aspect of the invention is a vector comprising a DNA sequence encoding, upon expression, a functional antagonist that contains the core physical structure comprising a hedgehog polypeptide lacking that N-terminal cysteine corresponding to Cys-1 of a mature hedgehog polypeptide and host cells containing the vector. In another aspect, the invention features a cell or purified preparation of cells which include a polynucleotide encoding, upon expression, a functional hedgehog antagonist. The cell preparation can consist of human or non human cells, e.g., mouse, hamster or rat cells, rabbit cells, monkey or pig cells. In preferred embodiments, the cell or cells include an antagonist transgene, e.g., a heterologous form of an antagonist gene. Therapeutic compositions are also intended to be encompassed by the invention. A therapeutic composition includes a functional antagonist polypeptide of the invention in combination with an acceptable carrier. Preferably, also included in the invention is a composition which includes an antagonist polypeptide and one or more additional components, e.g., a carrier, diluent, or solvent. The additional component can be one which renders the composition useful for in vitro, in vivo, pharmaceutical, or veterinary use.

Methods of making a functional hedgehog antagonist are a further aspect of the invention. One method comprises altering an N-terminal cysteine residue of a hedgehog polypeptide from a residue corresponding to residue Cys-1 of mature hedgehog polypeptide to a residue that does not correspond to Cys-1 of mature hedgehog polypeptide. This method may include the step of exposing isolated hedgehog polypeptide to proteolysis so that the resulting fragment does not contain the Cys-1.

Another method of making a functional hedgehog antagonist protein comprises expressing a functional antagonist protein from a host cell using DNA sequences and vectors of the invention and then purifying the expressed antagonist protein. A further method of making a functional hedgehog antagonist protein comprises expressing a hedgehog protein from a host cell using DNA sequences and vectors of the invention and then modifying the expressed protein to form an antagonist protein of the invention. The modifications may include addition of one or more chemical moieties to the hedgehog protein such as, but not limited to, polyethylene glycol (PEG) addition and addition of dextran.

A preferred therapeutic method of inhibiting hedgehog-dependent signaling in a subject comprises administering to the subject the therapeutic compositions of the invention. The preferred invention therefore features a method of treating a mammal, e.g., a human, at risk for a disorder, e.g., a disorder characterized by aberrant or unwanted level of hedgehog polypeptide. One gene therapy method includes administering to the mammal a treatment, e.g., an effective amount of an antagonist polypeptide-encoding polynucleotide. In another embodiment, the method includes administering to the mammal an effective amount of an antagonist polypeptide. In preferred embodiments, the disorder is one of a variety of hyperplastic and neoplastic transformations of cells of the central nervous system. Generally, antagonists of the invention are useful in regulating the functional performance of a wide range of cells, tissues and organs and have therapeutic uses ranging from neuroprotection, neuroregeneration and modulation of neural function. Further therapeutic compositions for use in gene therapy include vectors of the invention containing a functional antagonist transgene.

The antagonist polypeptide and polynucleotides are useful for: the production of peptides molecules which can modulate hedgehog activity, in vivo or in vitro; for analysis of hedgehog receptor activation; for the generation of anti-antagonist antibodies, which are useful for identifying cells which express antagonist or for evaluating levels of antagonist expression; for producing antagonist fragments of hedgehog, which can be used in vitro or in vivo to modulate hedgehog activity.

BRIEF DESCRIPTION OF THE DRAWINGS

Figure Legends

FIG. 1. Alignment of the N-terminal fragments of various human hedgehog proteins, consisting of human Indian, Sonic and Desert hedgehogs; SEQ ID NOS: 2, 3, and 4, respectively.

FIG. 2. C3H10T1/2 assay of Human sonic hedgehog N-terminal domain and variants. The activity of hu Shh and variants was assessed in the C3H10T1/2 assay measuring alkaline phosphatase induction. Serial 2-fold dilutions of Shh ( ■ ), Shh (C-9) (◇), Ihh (□), Dhh (△), his-tagged Shh (✕), Shh (N-5) (◀), Shh (N-9/C-3) (○), Shh (N-10) (+), Shh-N(C1S) (-) and Shh (N-8) (▲) were incubated with the cells for 5 days and the resulting levels of alkaline phosphatase activity (AP) measured at 405 nm using the AP chromogenic substrate p-nitrophenyl phosphate. The numbers presented reflect the averages of duplicate determinations.

FIG. 3. Analysis of Shh-N and truncated variants in a receptor binding assay. The relative potencies of Shh (■), Ihh (□), Dhh (△), his-tagged Shh (X). Shh (N-5) (♦), Shh (N-9/C-3) (○), Shh (N-10) (|), Shh (C1S) (-) and Shh (N-8) (▲) for binding to patched was assessed on patched transfected EBNA-293 cells by FACS analysis. Serial dilutions of the test samples were incubated with the EBNA-293 cells, washed and then the percent binding measured by the ability of the samples to compete with Shh-Ig from binding to the cells. Bound Shh-Ig was quantified by mean fluorescence. The data were fitted to a hyperbolic curve by non-linear regression.

FIG. 4. C3H10T1/2 blocking assay of Shh activity by Shh variants. The ability of Shh variants to block Shh induction of AP was assessed. Serial 2-fold dilutions of Dhh, Shh (N-5), Shh (N-10), Shh (N-9/C-3), his-tagged Shh-N and Shh (N-8)

were incubated with Shh (2 μg/ml) for 30 min and then subjected to analysis in the C3HT101/2 assay.

DESCRIPTION OF THE SEQUENCES

SEQ ID NO: 1 is a histagged Sonic hedgehog N-terminal domain fusion protein encoded by a cDNA subcloned into the pET11b vector as a six histidine-tagged fusion protein with an enterokinase cleavage site engineered into the construct immediately adjacent to Cys 1 of the mature Shh sequence.

```
MGSSHHHHHHSSGDDDDKCGPGRGFGKRRHPKKLTPLAYK
QFIPNVAEKTLGASGRYEGKISRNSERFKELTPNYNPDII
FKDEENTGADRLMTQRCKDKLNALAISVMNQWPGVKLRVT
EGWDEDGHHSEESLHYEGRAVDITTSDRDRSKYGMLARL
AVEAGFDWVYYESKAH IHCSVKAENSVAAKSGG
```

SEQ ID NO: 2 is the N-terminal fragment of human Indian hedgehog protein.

```
CGPGRVVGSRRRPPRKLVPLAYKQFSPNVPEKTLGASGR
YEGKIARSSERFKELTPNYNPDIIFKDEENTGADRLMTQR
CKDRLNSLAISVMNQWPGVKLRVTEGWDEDGHHSEESL
HYEGRAVDITTSDRDRNKYGLLARLAVEAGFDWVYYES
KAHVHCSVKSEHSAAAKTGG
```

SEQ ID NO: 3 is the N-terminal fragment of human Sonic hedgehog protein

```
CGPGRGFGKRRHPKKLTPLAYKQFIPNVAEKTLGASGRYE
GKISRNSERFKELTPNYNPDIIFKDEENTGADRLMTQRCK
DKLNALAISVMNQWPGVKLRVTEGWDEDGHHSEESLHY
EGRAVDITTSDRDRSKYGMLARLAVEAGFDWVYYESKAH
IHCSVKAENSVAAKSGG
```

SEQ ID NO: 4 is the N-terminal fragment of human Desert hedgehog protein

```
CGPGRGPVGRRRYARKQLVPLLYKQFVPGVPERTLGASGP
AEGRVARGSERFRDLVPNYNPDIIFKDEENSGADRLMTERC
KERVNALAIAVMNMWPGVRLRVTEGWDEDGHHAQDSLH
YEGRALDITTSDRDRNKYGLLARLAVEAGFDWVYYESRNH
VHVSVKADNSLAVRAGG
```

SEQ ID NO: 5 is a Sonic hedgehog functional antagonist lacking the first 10 N-terminal amino acids ("Shh(N-10)")

```
RHPKKLTPLAYKQFIPNVAEKTLGASGRYEGKISRNSERFKE
LTPNYNPDIIFKDEENTGADRLMTQRCKDKLNALAISVMNQW
PGVLRVTEGWDEDGHHSEESLHYEGRAVDITTSDRDRSKYG
MLARLAVEAGFDWVYYESKAHI HCSVKAENSVAAKSGG
```

SEQ ID NO: 6 is a Sonic hedgehog functional antagonist lacking the first 9 N-terminal amino acids and the last three C-terminal amino acids ("Shh (N-9, C-3)")

```
RRHPKKLTPLAYKQFIPNVAEKTLGASGRYEGKISRNSERFKE
LTPNYNPDIIFKDEENTGADRLMTQRCKDKLNALAISVMNQWP
GVKLRVTEGWDEDGHHSEESLHYEGRAVDITTSDRDRSKYGML
ARLAVEAGFDWVYYESKAHIHCSVKAENSVAAK
```

SEQ ID NO: 7 is a Sonic hedgehog functional antagonist lacking the first N-terminal amino acids ("Shh(N-5)")

```
GFGKRRHPKKLTPLAYKQFIPNVAEKTLGASGRYEGKISRNSERFK
ELTPNYNPDIIFKDEENTGADRLMTQRCKDKLNALAISVMNQWPG
VKLRVTEGWDEDGHHSEESLHYEGRAVDITTSDRDRSKYGMLARL
AVEAGFDWVYYESKAHIHCSVKAENSVAAKSGG
```

SEQ ID NO: 8 is a Sonic hedgehog functional antagonist whose N-terminal cysteine has been replaced with a Serine residue. ("C1S")

```
SGPGRGFGKRRHPKKLTPLAYKQFIPNVAEKTLGASGRYEGKISRNSE
RFKELTPNYNPDIIFKDEENTGADRLMTQRCKDKLNALAISVMNQWP
GVKLRVTEGWDEDGHHSEESLHYEGRAVDITTSDRDRSKYGMLARL
AVEAGFDWVYYESKAHIHCSVKAENSVAAKSGG
```

SEQ ID NO: 9 is the consensus sequence of an "N-10" hedgehog antagonist, where "Xaa" indicates amino acids that differ between the three proteins.

```
R R Xaa6 Xaa7 Xaa8 K Xaa9 L Xaa10 P    L Xaa11 Y K Q F Xaa12 P Xaa13 V
Xaa14 E K T L G A S G R                Xaa15 E G K Xaa16 Xaa17 R Xaa18 S E
R F K Xaa19 L Xaa20 P N Y N            P D I I F K D E E N
Xaa21 G A D R L M T Xaa22 R            C K Xaa23 Xaa24 Xaa25 N S L A I
Xaa26 V M N Xaa27 W P G V K            L R V T E G W D E D
G H H X2aa8 Xaa29 Xaa30 S L H Y        E G R A V D I T T S
D R D R Xaa31 K Y G Xaa32 L            A R L A V E A G F D
W V Y Y E S Xaa33 Xaa34 H Xaa35        H Xaa36 S V K Xaa37 Xaa38
Xaa39 S Xaa40                          A A Xaa41 Xaa42 G G
``` where

| | | |
|---|---|---|
| Xaa6 is either P, H or Y; | Xaa7 is either P or A; | Xaa8 is either R or K; |
| Xaa9 is any amino acid; | Xaa10 is either V or T; | Xaa11 is either A or L; |
| Xaa12 is either S, I or V; | Xaa13 is either N or G; | Xaa14 is either P or A; |
| Xaa15 is either Y or A; | Xaa16 is either I or V; | Xaa17 is either A or S; |
| Xaa18 is either S, N or G; | Xaa19 is either E or D; | Xaa20 is either T or V; |
| Xaa21 is either T or S; | Xaa22 is either Q or E; | Xaa23 is either D or E; |
| Xaa24 is either R or K; | Xaa25 is either L or V; | Xaa26 is either S or A; |
| Xaa27 is either Q or M; | Xaa28 is either S or A; | Xaa29 is either E or Q; |
| Xaa30 is either E or D; | Xaa31 is either N or S; | Xaa32 is either L or M; |
| Xaa33 is either K or R; | Xaa34 is either A or N; | Xaa35 is either V or I; |
| Xaa36 is either C or V; | Xaa37 is either S or A; | Xaa38 is either E or D; |
| Xaa39 is either H or N; | Xaa40 is either A, V or L; | Xaa41 is either K or R; and |
| Xaa42 is either T, S or A. | | |

SEQ ID NO: 10 is a Sonic hedgehog N-terminal domain variant ("Shh (C-9)") with the last 9 amino acids absent

CGPGRGFGKRRHPKKLTPLAYKQFIPNVAEKTLGASGRYEGKISRNSE

RFKELTPNYNPDIIFKDEENTGADRLMTQRCKDKLNALAISVMNQWP

GVKLRVTEGWDEDGHHSEESLHYEGRAVDITTSDRDRSKYGMLARL

AVEAGFDWVYYESKAHIHCSVKAE

SEQ ID NO: 11 is the "N-8" Sonic hedgehog antagonist ("Shh (N-8)")

KRRHPKKLTPLAYKQFIPNVAEKTLGASGRYEGKISRNSERFKELTPN

YNPDIIFKDEENTGADRLMTQRCKDKLNALAISVMNQWPGVKLRVTE

GWDEDGHHSEESLHYEGRAVDITTSDRDRSKYGMLARLAVEAGFDW

VYYESKAHIHCSVKAENSVAAKSGG

SEQ ID NO: 12 and 13 are nucleotide PCR primer pairs for ptc-1

5'-CATTGGCAGGAGGAGTTGATTGTGG-3'   (SEQ ID NO: 12)

5'-AGCACCTTTTGAGTGGAGTTTGGGG-3'   (SEQ ID NO: 13)

SEQ ID NO: 14 and 15 are nucleotide PCR primer pairs for gli-1

5'-CGGGGTCTCAAACTGCCCAGCTT-3'   (SEQ ID NO: 14)

5'-GGCTGGGTCACTGGCCCTC-3'   (SEQ ID NO: 15)

SEQ ID NO: 16 is the DNA sequence of mature ("N-10") Sonic Hedgehog

```
  1 AGGCACCCCAAAAAGCTGACCCCTTTAGCCTACAAGCAGTTTATCCCCAATGTGGCCGAG
 61 AAGACCCTAGGCGCCAGCGGAAGGTATGAAGGGAAGATCTCCAGAAACTCCGAGCGATTT
121 AAGGAACTCACCCCCAATTACAACCCCGACATCATATTTAAGGATGAAGAAAACACCGGA
181 GCGGACAGGCTGATGACTCAGAGGTGTAAGGACAAGTTGAACGCTTTGGCCATCTCGGTG
241 ATGAACCAGTGGCCAGGAGTGAAACTGCGGGTGACCGAGGGCTGGGACGAAGATGGCCAC
301 CACTCAGAGGAGTCTCTGCACTACGAGGGCCGCGCAGTGGACATCACCACGTCTGACCGC
361 GACCGCAGCAAGTACGGCATGCTGGCCCGCCTGGCGGTGGAGGCCGGCTTCGACTGGGTG
421 TACTACGAGTCCAAGGCACATATCCACTGCTCGGTGAAAGCAGAGAACTCGGTGGCGGCC
481 AAATCGGGAGGC 492
```

SEQ ID NO: 17 is the DNA sequence of mature "C1S" Sonic Hedgehog

```
  1 TCGGGCCCGGGCAGGGGGTTCGGGAAGAGGAGGCACCCCAAAAAGCTGACCCCTTTAGCC
 62 TACAAGCAGTTTATCCCCAATGTGGCCGAGAAGACCCTAGGCGCCAGCGGAAGGTATGAA
121 GGGAAGATCTCCAGAAACTCCGAGCGATTTAAGGAACTCACCCCCAATTACAACCCCGAC
181 ATCATATTTAAGGATGAAGAAAACACCGGAGCGGACAGGCTGATGACTCAGAGGTGTAAG
241 GACAAGTTGAACGCTTTGCCCATCTCGGTGATGAACCAGTGGCCAGGAGTGAAACTGCGG
301 GTGACCGAGGGCTGGGACGAAGATGGCCACCACTCAGAGGAGTCTCTGCACTACGAGGGC
```

-continued

```
361 CGCGCAGTGGACATCACCACGTCTGACCGCGACCGCAGCAAGTACGGCATGCTGGCCCGC

421 CTGGCGGTGGAGGCCGGCTTCGACTGGGTGTACTACGAGTCCAAGGCACATATCCACTGC

481 TCGGTGAAAGCAGAGAACTCGGTGGCGGCCAAATCGGGAGGC 522
```

SEQ ID NO: 18 and 19 are oligonucleotide ligation sequences.

```
                                        SEQ ID NO: 18
  5' TCG AGA AAA GAT GCG GAC CGG GCA GGG GGT 3':

SEQ ID NO: 19
  5' CGA ACC CCC TGC CCG GTC CGC ATC TTT TC 3':
```

DETAILED DESCRIPTION OF THE INVENTION

I. Definitions

The invention will now be described with reference to the following detailed description of which the following definitions are included:

"amino acid"—a monomeric unit of a peptide, polypeptide, or protein. There are twenty amino acids found in naturally occurring peptides, polypeptides and proteins, all of which are L-isomers. The term also includes analogs of the amino acids, modified amino acid residues, and D-isomers of the protein amino acids and their analogs.

"protein"—any polymer consisting essentially of any of the amino acids. Although "polypeptide" is often used in reference to relatively large polypeptides, and "peptide" is often used in reference to small polypeptides, usage of these terms in the art overlaps and is varied. The term "protein" as used herein refers to peptides, proteins and polypeptides, unless otherwise noted.

"N-terminal end"—refers to the first amino acid (amino acid number 1) of the mature form of a protein, the "mature form" of a protein comprising the primary amino acid sequence after removal of any signal, or other sequence.

"N-terminal cysteine" refers to any cysteine that occupies the N-terminal end of a hedgehog protein. Cys-1 of the "mature" Sonic hedgehog N-terminal fragment (amino acid residue number 1 of SEQ ID NO: 3) corresponds to residue number 24 of the Sonic hedgehog gene sequence as amino acid residues 1-23 encoded by the gene sequence comprise the signal region and are removed to form the "mature" protein. In particular, an "N-terminal cysteine" occupies the same position in a hedgehog polypeptide that it occupies in the human Sonic hedgehog polypeptide sequence. Specifically, "N-terminal cysteine" refers to the amino acid residue number 1 as the first amino acid residue in SEQ ID NOS: 24. It will be understood that the N-terminal cysteine of other hedgehog proteins may not correspond exactly to the Cys-1 of mature Sonic hedgehog. For example, due to differing lengths and sequences of the signal sequences, the cysteine at residue number 24 of sonic hedgehog sequence (Cys-1 of the mature form [SEQ ID NO:3] after removal of the signal sequence) corresponds to the cysteine at residue number 28 (the first amino acid residue in SEQ ID NO: 2) of Indian hedgehog and to the cysteine at residue number 23 (the first amino acid residue in SEQ ID NO: 4) of Desert hedgehog. Maximal homology of these proteins is obtained by aligning these cysteines which are Cys-1 in the mature protein, as shown in FIG. 1. Nevertheless, persons having ordinary skill in the art will appreciate that exact residue number of any given "N-terminal cysteine" of the mature protein may vary slightly among different members of the hedgehog family of proteins. Further, persons having ordinary skill in the art will be able to determine which residue of a given hedgehog polypeptide is in fact the N-terminal residue. The present invention is not intended to be limited by this variability.

"N-terminal extension moiety" refers to a 5' extension from the N-terminal cysteine and includes at least one individual unit (an "element"). One of the elements (e.g., an amino acid residue) of an N-terminal extension moiety may replace the N-terminal cysteine of a mature hedgehog polypeptide.

"functional antagonist" refers to an agent (e.g., a hedgehog protein) that is capable of inhibiting the in vitro or in vivo functioning of a protein. Further, the term includes a hedgehog protein that is inactive at eliciting a hedgehog-dependent response on C3H 10 T1/2 cells, but competes with hedgehog for binding to the hedgehog receptor.

"fragment", as applied to an isolated antagonist, can be as small as a single amino acid provided that it retains antagonist activity. It may be at least about 10 residues, more typically at least about 40 residues, preferably at least about 100 residues in length. Fragments can be generated by methods known to those skilled in the art. The ability of a candidate fragment to exhibit isolated hedgehog biological activity can be also assessed by methods known to those skilled in the art as described herein.

"functional equivalent" of a hedgehog antagonist of the invention is an agent that may have different amino acid residues as the hedgehog antagonist but acts as a functional antagonist nonetheless.

"genetic fusion"—refers to a co-linear, covalent linkage of two or more proteins or fragments thereof via their individual peptide backbones, through genetic expression of a polynucleotide molecule encoding those proteins.

"mutant"—any change in the genetic material of an organism, in particular any change (i.e., deletion, substitution, addition, or alteration) in a wild-type polynucleotide sequence or any change in a wild-type protein.

"wild-type"—the naturally-occurring polynucleotide sequence of an exon of a protein, or a portion thereof, or protein sequence, or portion thereof, respectively, as it normally exists in vivo.

"mature" hedgehog protein—"mature" refers to a wild-type sequence comprising the processed N-terminal domain. For example, human Sonic hedgehog (Shh) residues 24-197, human Indian hedgehog (Ihh) residues 23-197, human Desert hedgehog (Dhh) residues 28-203. While the natural form of the mature hedgehog protein is post-translationally modified, some of the recombinant versions used herein lack these modifications but are still active and are referred to as mature.

The term "polynucleotide sequence" and "nucleotide sequence" are used interchangeably and, as used herein, can include fragments and equivalents. The term "equivalent" refers to nucleotide sequences encoding functionally equivalent polypeptides. "Equivalent" nucleotide sequences will include sequences that differ by one or more nucleotide substitutions, additions or deletions, such as allelic variants, and include sequences that differ from the nucleotide sequences encoding the hedgehog antagonists of the invention, due to the degeneracy of the genetic code.

"standard hybridization conditions"—salt and temperature conditions substantially equivalent to 0.5×SSC to about 5×SSC and 65° C. for both hybridization and wash. The term "standard hybridization conditions" as used herein is therefore an operational definition and encompasses a range of hybridization conditions. Higher stringency conditions may, for example, include hybridizing with plaque screen buffer (0.2% polyvinylpyrrolidone, 0.2% Ficoll 400; 0.2% bovine serum albumin, 50 mM Tris-HCl (pH 7.5); 1 M NaCl; 0.1% sodium pyrophosphate; 1% SDS); 10% dextran sulphate, and 100 (g/ml denatured, sonicated salmon sperm DNA at 65° C. for 12-20 hr, and washing with 75 mM NaCl/7.5 mM sodium citrate (0.5×SSC)/1% SDS at 65° C. Lower stringency conditions may, for example, include hybridizing with plaque screen buffer, 10% dextran sulphate and 110 (g/ml denatured, sonicated salmon sperm DNA at 55° C., for 12-20 hr, and washing with 300 mM NaCl/30 mM sodium citrate (2.0× SSC)/1% SDS at 55° C. See also Current Protocols in Molecular Biology, John Wiley & Sons, Inc. New York, Sections 6.3.1-6.3.6, (1989).

"expression control sequence"—a sequence of polynucleotides that controls and regulates expression of genes when operatively linked to those genes.

"operatively linked"—a polynucleotide sequence (DNA, RNA) is operatively linked to an expression control sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the polynucleotide sequence under the control of the expression control sequence and production of the desired polypeptide encoded by the polynucleotide sequence.

"expression vector"—a polynucleotide, such as a DNA plasmid or phage (among other common examples) which allows expression of at least one gene when the expression vector is introduced into a host cell. The vector may, or may not, be able to replicate in a cell.

"Isolated" (used interchangeably with "substantially pure")—when applied to polynucleotide i.e., polynucleotide sequences, that encode polypeptides, means an RNA or DNA polynucleotide, portion of genomic polynucleotide, cDNA or synthetic polynucleotide which, by virtue of its origin or manipulation: (i) is not associated with all of a polynucleotide with which it is associated in nature (e.g., is present in a host cell as an expression vector, or a portion thereof); or (ii) is linked to a polynucleotide or other chemical moiety other than that to which it is linked in nature; or (iii) does not occur in nature. By "isolated" it is further meant a polynucleotide sequence that is: (i) amplified in vitro by, for example, polymerase chain reaction (PCR); (ii) chemically synthesized; (iii) recombinantly produced by cloning; or (iv) purified, as by cleavage and gel separation. Thus, "substantially pure polynucleotide" is a polynucleotide which is not immediately contiguous with one or both of the coding sequences with which it is normally contiguous in the naturally occurring genome of the organism from which the polynucleotide is derived. Substantially pure DNA also includes a recombinant DNA which is part of a hybrid gene encoding additional hedgehog sequences.

"Isolated" (used interchangeably with "substantially pure")—when applied to polypeptides means a polypeptide or a portion thereof which, by virtue of its origin or manipulation: (i) is present in a host cell as the expression product of a portion of an expression vector; or (ii) is linked to a protein or other chemical moiety other than that to which it is linked in nature; or (iii) does not occur in nature. By "isolated" it is further meant a protein that is: (i) chemically synthesized; or (ii) expressed in a host cell and purified away from associated proteins. The term generally means a polypeptide that has been separated from other proteins and polynucleotides with which it naturally occurs. Preferably, the polypeptide is also separated from substances such as antibodies or gel matrices (polyacrylamide) which are used to purify it.

"heterologous promoter"—as used herein is a promoter which is not naturally associated with a gene or a purified polynucleotide.

"Homologous"—as used herein is synonymous with the term "identity" and refers to the sequence similarity between two polypeptides, molecules or between two polynucleotides. When a position in both of the two compared sequences is occupied by the same base or amino acid monomer subunit (for instance, if a position in each of the two DNA molecules is occupied by adenine, or a position in each of two polypeptides is occupied by a lysine), then the respective molecules are homologous at that position. The percentage homology between two sequences is a function of the number of matching or homologous positions shared by the two sequences divided by the number of positions compared× 100. For instance, if 6 of 10 of the positions in two sequences are matched or are homologous, then the two sequences are 60% homologous. By way of example, the DNA sequences CTGACT and CAGGTT share 50% homology (3 of the 6 total positions are matched). Generally, a comparison is made when two sequences are aligned to give maximum homology. Such alignment can be provided using, for instance, the method of Needleman et al., J. Mol Biol. 48: 443-453 (1970), implemented conveniently by computer programs such as the Align program (DNAsta, Inc.). Homologous sequences share identical or similar amino acid residues, where similar residues are conservative substitutions for, or "allowed point mutations" of, corresponding amino acid residues in an aligned reference sequence. In this regard, a "conservative substitution" of a residue in a reference sequence are those substitutions that are physically or functionally similar to the corresponding reference residues, e.g., that have a similar size, shape, electric charge, chemical properties, including the ability to form covalent or hydrogen bonds, or the like. Particularly preferred conservative substitutions are those fulfilling the criteria defined for an "accepted point mutation" in Dayhoff et al., 5: Atlas of Protein Sequence and Structure, 5: Suppl. 3, chapter 22: 354-352, Nat. Biomed. Res. Foundation, Washington, D.C. (1978).

A "hedgehog protein" of the invention is defined in terms of having at least a portion that consists of SEQ ID NOS: 2-4. The term also means a hedgehog polypeptide, or a functional variant of a hedgehog polypeptide or homolog of a hedgehog polypeptide or functional variant which has biological activity.

The terms "peptide(s)", "protein(s)" and "polypeptide(s)" are used interchangeably herein. The terms "polynucleotide sequence" and "nucleotide sequence" are also used interchangeably herein. The term "Hedgehog fragment" is used interchangeably with "Hedgehog".

A hedgehog molecule has "biological activity" if it has at least one of the following properties: (i) the molecule meets the hedgehog consensus criteria as defined herein (SEQ ID NO: 4) and has the ability to bind to its receptor, patched-1 or it encodes, upon expression, a polypeptide that has this characteristic; (ii) the molecule meets the hedgehog consensus criteria as defined herein or it encodes, upon expression, a polypeptide that has this characteristic; and (iii) it induces alkaline phosphatase activity in C3H 10 T1/2 cells Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, Molecular Cloning: A Laboratory Manual, 2nd edition. (Sambrook, Fritsch and Maniatis, eds.), Cold Spring Harbor Laboratory Press, 1989; DNA Cloning, Volumes I and II (D. N. Glover, ed), 1985; Oligonucleotide Synthesis, (M. J. Gait, ed.), 1984; U.S. Pat. No. 4,683,195 (Mullis et al.,); Polynucleotide Hybridization (B. D. Hames and S. J. Higgins, eds.), 1984; Transcription and Translation (B. D. Hames and S. J. Higgins, eds.), 1984; Culture of Animal Cells (R. I. Freshney, ed). Alan R. Uss, Inc., 1987; Immobilized Cells and Enzymes, MRL Press, 1986; A Practical Guide to Molecular Cloning (B. Perbal), 1984; Methods in Enzymology, Volumes 154 and 155 (Wu et al., eds), Academic Press, New York; Gene Transfer Vectors for Mammalian Cells (J. H. Miller and M. P. Calos, eds.), 1987, Cold Spring Harbor Laboratory; Immunochemical Methods in Cell and Molecular Biology (Mayer and Walker, eds.), Academic Press, London, 1987; Handbook of Experiment Immunology, Volumes I-IV (D. M. Weir and C. C. Blackwell, eds.), 1986; Manipulating the Mouse Embryo, Cold Spring Harbor Laboratory Press, 1986.

Other features and advantages of the invention will be apparent from the following detailed description, and from the claims. Unless indicated otherwise, all references cited in the Detailed Description of the Invention are incorporated herein by reference. None of the references in the Background are admitted to be prior art.

II. General Properties of Hedgehog Proteins

The functional antagonists of the present invention are obtainable from isolated hedgehog proteins. Thus, Sonic, Indian or Desert may be converted into functional antagonists.

Isolated hedgehog proteins are naturally occurring or recombinant proteins of the hedgehog family and may be obtainable from either invertebrate or vertebrate sources (see references below). Members of the vertebrate hedgehog protein family share homology with proteins encoded by the Drosophila hedgehog (hh) gene (Mohler and Vani, (1992) Development 115, 957-971). To date, the combined screening of mouse genomic and cDNA libraries has identified three mammalian hh counterparts referred to as Desert hedgehog (Dhh), Sonic hedgehog (Shh) and Indian hedgehog (Ihh), which also exist in other mammals such as humans as well as in fish and birds. Other members include Moonrat hedgehog (Mhh), as well as Tiggy-winkle hedgehog (TwHh) and echidna hedgehog (Ehh).

Hedgehog genes encode glycoproteins which undergo cleavage, yielding an N-terminal domain of about 20 kDa responsible for signaling (See SEQ ID NOS: 2-4 and FIG. 1) and a carboxy terminal fragment of about 25 kDa. Various other fragments that encompass the 20 kDa moiety are considered within the definition of "isolated hedgehog protein". Publications disclosing these sequences, as well as their chemical and physical properties, include (Hall et al., (1995) Nature 378, 212-216; Ekker et al., (1995) Current Biology 5, 944-955; Fan et al., (1995) Cell 81, 457-465, Chang et al., (1994) Development 120, 3339-3353; Echelard et al., (1993) Cell 75, 1414-1430 34-38); PCT Patent Application WO 9523223 (Jessell, Dodd, Roelink and Edlund).

Hedgehog family members include any of the naturally-occurring native hedgehog proteins including allelic, phylogenetic counterparts or other variants thereof, whether naturally-sourced or chemically produced including muteins or mutant proteins, as well as recombinant forms and new, active members of the hedgehog family. Particularly useful hedgehog polypeptides suitable for developing antagonists include SEQ ID NOS: 2-4.

III. Hedgehog Antagonists

The most preferred polypeptides of the invention are antagonists of a biological activity of the naturally occurring or recombinant hedgehog protein (e.g., an isolated hedgehog such as a member of the vertebrate family obtainable from Sonic, Indian or Desert hedgehog protein described above). The functional antagonists have at least the following properties: (i) the isolated protein binds the receptor patched-1 with an affinity that may be less than, but is preferably at least the same as, the binding of mature hedgehog protein to patched-1; and (ii) the isolated protein blocks alkaline phosphatase (AP) induction by mature hedgehog protein when tested in an in vitro CH310T1/2 cell-based AP induction assay. Antagonists of the invention may also have the additional properties of being (iii) unable to induce ptc-1 and gli-1 expression.

Persons having ordinary skill in the art can easily test any putative hedgehog antagonist for these properties. In particular, the mouse embryonic fibroblast line C3H10T1/2 is a mesenchymal stem cell line that is hedgehog responsive. Hedgehog treatment of the cells causes an upregulation of gli-1 and patched-1 (known indicators of hedgehog dependent signaling) and also causes induction of alkaline phosphatase activity, an indicator that the cells have differentiated down the chondrocyte/bone osteoblast lineage. We developed and studied a panel of several hedgehog variants and discovered that certain variants not only were inactive at eliciting a hedgehog-dependent response on C3H10T1/2 cells, but they competed with mature hedgehog for function and therefore served as functional antagonists.

A. N-Modified Hedgehog Polypeptides as Antagonists

We have discovered that certain hedgehog variants that contain N-terminal modifications can block hedgehog function because they lack the ability to elicit a hedgehog-dependent response but retain the ability to bind to hedgehog receptor, patched-1.

The critical primary amino acid sequence that defines whether a hedgehog polypeptide (i.e., a Sonic, Indian or Desert hedgehog) is a functional hedgehog antagonist is the N-terminal cysteine residue which corresponds to Cys-1 of the mature hedgehog (See FIG. 1). So long as the hedgehog polypeptide either lacks this N-terminal cysteine completely or contains this N-terminal cysteine in a modified form (e.g. chemically modified or included as part of an N-terminal extension moiety), the resulting polypeptide can act as a functional hedgehog antagonist. In this regard, the fact that an N-terminal cysteine "corresponds to Cys-1" means: (a) the N-terminal cysteine is the Cys-1 of mature Sonic, Indian or Desert hedgehog; or (b) the N-terminal cysteine occupies the same position as Cys-1 of mature Sonic, Indian or Desert hedgehog. Provided that, for example, a Sonic hedgehog has an N-terminal cysteine corresponding to Cys-1 that is altered or otherwise modified as described herein, it can antagonize the action of any other member is of the hedgehog family. We have generated a Sonic hedgehog protein that antagonizes the action of Sonic and Indian hedgehog and have generated a Desert hedgehog protein that antagonizes the action of Sonic hedgehog. Therefore, persons having ordinary skill in the art will understand that it is possible to develop according to the rules set out in this invention, an Indian hedgehog protein that antagonizes the activity of Sonic, Desert or Indian hedgehogs.

We provide examples of these N-terminal modifications and one skilled in the art can alter the disclosed structure of the antagonist, e.g., by producing fragments or analogs, and test the newly produced structures for antagonist activity. Examples of prior art methods which allow the production and testing of fragments and analogs are discussed below. These, or analogous methods, can be used to make and screen fragments and analogs of a antagonist polypeptides. There are several variants that are included in the invention.

1. N-Terminal Extensions

Antagonist polypeptides of the invention may include a hedgehog polypeptide sequence in which the N-terminal cysteine is linked to an N-terminal extension moiety. The isolated antagonist polypeptide can therefore be, as but one example, a recombinant fusion protein having: (a) a first N-terminal polypeptide portion that can be 5' to the hedgehog polypeptide itself, and that contains at least one element (e.g., an amino acid residue) that may be unrelated to hedgehog, linked to (b) an N-terminal cysteine corresponding to Cys-1 of Sonic hedgehog that is part of a hedgehog antagonist of the invention, or a portion of hedgehog antagonist. This N-terminal extension moiety (e.g., the first N-terminal polypeptide portion) can be a histidine tag, a maltose binding protein, glutathione-S-transferase, a DNA binding domain, or a polymerase activating domain. The functional antagonist may include an N-terminal extension moiety that contains an element which replaces the Cys-1 of mature hedgehog or an N-terminal cysteine that corresponds to Cys-1 of a mature Sonic hedgehog. Such an antagonist is represented by SEQ ID NO: 1 in which the Cys-1 is itself unmodified but is linked to an element (i.e., an amino acid residue) as part of an N-terminal extension moiety. Without wishing to be bound by any theory, we believe that the antagonist properties of this protein are because the N-terminal extension moiety (the his tag) prevents the N-terminal cysteine from functioning as it would in the absence of the extension moiety.

2. N-Terminal Deletions

In another embodiment, the functional antagonist is missing no greater than about 12 amino acids beginning from that N-terminal cysteine corresponding to Cys-1 of a mature hedgehog. We have found that deletions in more than the about the first 12 contiguous amino acid residues do not generate functional antagonists. Preferably, deletions of about 10 contiguous amino acids will provide suitable functional antagonists. We can, however, remove fewer than 10 contiguous residues and still maintain antagonist function. Moreover, we can delete various combinations of non-contiguous residues provided that there are at least about 3 deleted residues in total.

Here we describe several such Sonic hedgehog antagonists: Shh ("N-10") (SEQ ID NO: 5: lacking the first 10 amino acids of the N-terminal domain); Shh ("N-9, C-3") (SEQ ID NO: 6: lacking the first nine amino acid residues beginning from the N-terminal cysteine and lacking the last 3 residues from the C-terminal end.); Shh ("N-5") (SEQ ID NO: 7: lacking the first five amino acid residues beginning from the N-terminal cysteine).

These structures highlight the importance of the N-terminus of hedgehog proteins for function. All of the variants were indistinguishable from mature Sonic hedgehog (Shh) in their ability to bind patched-1, but were inactive in the in vitro C3H10T1/2 AP induction assay. The "N-10" (SEQ ID NO: 5) variant was also tested for its ability to induce ptc-1 and gli-1 expression and was inactive. All these N-terminal variants are unable to promote hedgehog-dependent signaling.

3. N-Terminal Mutations

In yet another embodiment, the functional antagonist has a mutation of the N-terminal cysteine to another amino acid residue. Any amino acid residue may acceptable and persons having ordinary skill in the art following the teachings described herein will be able to perform the mutations and test the effects of such mutations. One example is Shh ("C1S") (SEQ ID NO: 8) in which the N-terminal cysteine is replaced with a serine residue. This mutated form is indistinguishable from mature Shh in its ability to bind patched-1, but it blocks AP induction by mature Shh when tested for function in the C3H10T1/2 AP induction assay. SEQ ID NO: 8 was also tested for its ability to induce ptc-1 and gli-1 expression and is inactive.

4. N-Terminal Cysteine Modifications

Because the primary amino acid sequence of hedgehog contains the Cys-1 that is important for biological activity, we expect that certain other modifications will result in inactive antagonist variants of hedgehog protein. Another aspect of the invention is an isolated functional antagonist of a hedgehog polypeptide, comprising a hedgehog polypeptide containing an N-terminal cysteine that corresponds to Cys-1 of a mature Sonic hedgehog, except that the cysteine is in a modified form. Antagonist polypeptides of the invention may have non-sequence modifications that include in vivo or in vitro chemical derivatization of their N-terminal cysteine, as well as possible changes in acetylation, methylation, phosphorylation, amidation, carboxylation or glycosylation. As an example, the functional antagonist can have an N-terminal cysteine in an oxidized form. We have shown that the functional antagonist can have an N-terminal cysteine that is effectively modified by including it as part of an N-terminal extension moiety.

B. Other Embodiments

The antagonist polypeptides of the invention can include amino acid sequences that are at least 60% homologous to an amino acid sequence from SEQ ID NOS. 1-8 and 11. The antagonist polypeptides can include at least 100 contiguous amino acids from SEQ ID NOS: 1-4, 5-8 and 11. The antagonist polypeptide exhibits at least the following functional antagonist properties: (i) the isolated protein binds the receptor patched-1 with an affinity that may be less than, but is preferably at least the same as, the binding of mature hedgehog protein to patched-1; and (ii) the isolated protein blocks alkaline phosphatase (AP) induction by mature hedgehog protein when tested in an in vitro CH310T1/2 cell-based AP induction assay.

Polypeptides of the invention include those which arise as a result of the existence of multiple genes, alternative transcription events, alternative RNA splicing events, and alternative translational and posttranslational events. The polypeptide can be made entirely by synthetic means or can be expressed in systems, e.g., cultured cells, which result in substantially the same posttranslational modifications present when the protein is expressed in a native cell, or in systems which result in the omission of posttranslational modifications present when expressed in a native cell.

In a preferred embodiment, isolated antagonist is a polypeptide with one or more of the following characteristics:

(i) it has at least 60, more preferably 90 and most preferably 95% sequence identity with amino acids of SEQ ID NOS: 2-8;

(ii) it either has a modified N-terminal cysteine or lacks an N-terminal cysteine or has an N-terminal cysteine in a position different from the N-terminal cysteine corresponding to Cys-1 of the hedgehog;

(iii) it blocks alkaline phosphatase induction by mature hedgehog in CH310T1/2 cells;

(iv) it binds or interacts with its receptor patched-1 with an affinity that may be less than, but is preferably at least the same as, the binding of mature hedgehog protein to patched-1;

(v) it is unable to induce ptc-1 and gli-1 expression in vitro in CH310T1/2 cells;

(vi) it is unable to induce AP in CH310T 1/2 assays.

Moreover, the isolated hedgehog antagonists of the invention can also be a recombinant fusion protein containing additional C-terminal sequences unrelated to hedgehog. Thus, the antagonist polypeptide may also include all or a fragment of an amino acid sequence from SEQ ID NOS: 1-4 and 5-8, fused, in reading frame, to additional amino acid residues. One version of the polypeptides of the invention is a protein having a first polypeptide portion and a hedgehog antagonist portion, the antagonist portion being fused or otherwise linked either 5' or 3' to the first polypeptide portion. Thus, first, additional polypeptide portion has an amino acid sequence unrelated to an antagonist polypeptide. The additional polypeptide portion can be, e.g., any of glutathione-S-transferase, a DNA binding domain, or a polymerase activating domain, a histidine tag, an immunoglobulin or portion thereof, fused or otherwise linked to either the N- or C-terminus of the antagonist portion. Additional modified polypeptides include those that contain chemical moieties such as polyethylene glycol (PEG) and/or dextran, among others. The addition of such chemical moieties may be specific to the N-terminal cysteine or may involve linkages to other amino acid residues of the antagonist polypeptide. Moieties such as PEG or dextran, or constructs such as immunoglobulin fusions, may serve to increase the effective half life of the antagonist proteins when they are used as therapeutics.

IV. Expression and Production of Antagonist Polypeptides

It will be understood by persons having ordinary skill in the art that full length hedgehog polypeptides and antagonist polypeptides described herein can be produced by any suitable method known in the art. Such methods range from direct protein synthetic methods to constructing a DNA sequence directly encoding antagonist polypeptide sequences described above and expressing those antagonist sequences in a suitable transformed host. Alternatively, functional antagonist polypeptides of the invention may be developed by expressing full-length hedgehog proteins and then modifying them appropriately after expression to form the functional antagonist.

A. Direct Expression of Functional Antagonists

Generally, to produce a hedgehog sequence (whether or not an antagonist) a complete hedgehog amino acid sequence may be used to construct a back-translated gene. See Maniatis et al., supra. Further, a DNA oligomer containing a nucleotide sequence coding for full length hedgehog may be synthesized. For example, several small oligonucleotides coding for portions of the desired hedgehog polypeptide may be synthesized and then ligated. The individual oligonucleotides typically contain 5' or 3' overhangs for complementary assembly. Hedgehog cDNA may be obtained by screening a human cDNA library with a labeled DNA fragment encoding the hedgehog polypeptides of SEQ ID NOS: 1-8 and 11 and identifying positive clones by autoradiography. Further rounds of plaque purification and hybridization are performed using conventional methods.

If a DNA sequence is obtained encoding full length hedgehog polypeptide, the DNA may then be modified or mutagenized (see, e.g., Section C and D; Zoeller et al., (1984) Proc. Natl. Acad. Sci. USA, 81, 5662-66, and U.S. Pat. No. 4,588,585)) so as to express a functional antagonist polypeptide. In recombinant methods, internal or terminal fragments of a hedgehog polypeptide can be generated by removing one or more nucleotides from one end (for a terminal fragment) or both ends (for an internal fragment) of a DNA sequence which encodes for the isolated hedgehog polypeptide. Expression of the mutagenized DNA produces polypeptide fragments that are tested for biological activity. Digestion with "end nibbling" endonucleases can also generate DNAs which encode an array of fragments. DNAs which encode fragments of a protein can also be generated by random shearing, restriction digestion or a combination or both. Another method of constructing a similar DNA sequence would be by chemical synthesis using an oligonucleotide synthesizer. Such oligonucleotides may be preferably designed based on the amino acid sequence of the desired polypeptide, and preferably selecting those codons that are favored in the host cell in which the recombinant polypeptide of interest will be produced.

Therefore, isolated polynucleotides (e.g., RNA or DNA) are encompassed within the invention. These include SEQ ID NOS: 16 and 17 and those sequence encoding SEQ ID NOS: 1-8 and 11 Isolated polynucleotides of the invention may encode functional hedgehog antagonists that include a hedgehog polypeptide sequence in which the N-terminal cysteine is replaced by an N-terminal extension moiety. The isolated DNA sequence can therefore encode, as but one example, a recombinant fusion protein having: (a) a first N-terminal polypeptide portion that can be 5' to the hedgehog polypeptide itself, and that contains at least one element (e.g., an amino acid residue) that may be unrelated to hedgehog and that replaces the N-terminal cysteine of hedgehog; linked to (b) a second polypeptide that is a hedgehog antagonist, or a portion of hedgehog antagonist. Isolated polynucleotides of the invention also may encode for a functional antagonist that includes an N-terminal extension moiety that may contains the Cys-1 of a mature hedgehog polypeptide (e.g., Sonic hedgehog).

The isolated DNA sequence may encode, upon expression, a functional antagonist that contains the primary amino acid sequence comprising a hedgehog polypeptide lacking that N-terminal cysteine corresponding to Cys-1 of a mature hedgehog, such as, for instance, mature Sonic hedgehog. For example, the isolated DNA sequence or a portion thereof (e.g., SEQ ID NO; 16) can encode a functional antagonist that has a deletion of no greater than about 12 amino acids beginning from that N-terminal cysteine corresponding to Cys-1 of mature Sonic hedgehog (see SEQ ID NOS: 5-7). Isolated polynucleotides (e.g., SEQ ID NO: 17) of the invention may also be generated that encode a functional antagonist that has a mutation of the N-terminal cysteine to another amino acid residue. The isolated DNA sequence can also encode a functional antagonist that includes an N-terminal extension moiety (SEQ ID NO: 1).

Preferred DNA sequences encoding a functional antagonist of a hedgehog polypeptide include a polynucleotide selected from the group consisting of: (a) SEQ ID NOS.: 16 and 17; (b) a polynucleotide that hybridizes to any of the foregoing sequences under standard hybridization conditions and that encodes a protein having the activity of a functional antagonist of a hedgehog polypeptide; and (c) a polynucleotide that codes on expression for a protein encoded by any of the foregoing polynucleotide sequences. Moreover, the polynucleotides which encode antagonist polypeptides of the invention, also hybridize under standard conditions to a polynucleotide probe corresponding to at least 12 consecutive nucleotides from SEQ ID NOS: 16 and 17, more preferably to at least consecutive nucleotides from SEQ ID NOS: 16 and 17.

Once assembled (by synthesis, site-directed mutagenesis or another method), the DNA sequences encoding a particular isolated polypeptide of interest will be inserted into an expression vector and operatively linked to an expression control sequence appropriate for expression of the protein in a desired host. Proper assembly may be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

The choice of expression control sequence and expression vector will depend upon the choice of host. A wide variety of expression host/vector combinations may be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Esherichia coli*, including pCR1, pBR322, pMB9 and their derivatives, wider host range plasmids, such as M13 and filamentous single-stranded DNA phages. Preferred *E. coli* vectors include pL vectors containing the lambda phage pL promoter (U.S. Pat. No. 4,874,702), pET vectors containing the 17 polymerase promoter (Studier et al., Methods in Enzymology 185: 60-89, 1990 1) and the pSP72 vector. Useful expression vectors for yeast cells, for example, include the centromere plasmids.

In addition, any of a wide variety of expression control sequences may be used in these vectors. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda (for example pL), the control regions of fd coat protein, the promoter for 3-phosphoglycerate kinase or other glycolytic enzymes, the promoters of acid phosphatase, e.g., Pho5, the promoters of the yeast alpha-mating system and other sequences known to control the expression of genes of prokaryotic or eukaryotic cells and their viruses, and various combinations thereof. Any suitable host may be used to produce in quantity the isolated hedgehog polypeptides described herein, including bacteria, fungi (including yeasts), plants, insects, mammals, or other appropriate animal cells or cell lines, as well as transgenic animals or plants. More particularly, these hosts may include well known eukaryotic and prokaryotic hosts, such as strains of *E. coli*, (Example 1), *Pseudomonas, Bacillus, Streptomyces*, fungi, yeast (e.g., *Pichia*; Example 3) insect cells such as *Spodoptera frugiperda* (SF9), and High Five™, animal cells such as Chinese hamster ovary (CHO), mouse cells such as NS/O cells, African green monkey cells COS1, COS 7, BSC 1, BSC 40, and BMT 10, and human cells, as well as plant cells.

It should be understood that not all vectors and expression control sequences will function equally well to express a given isolated polypeptide. Neither will all hosts function equally well with the same expression system. However, one of skill in the art may make a selection among these vectors, expression control systems and hosts without undue experimentation. For example, to produce isolated polypeptide of interest in large-scale animal culture, the copy number of the expression vector must be controlled. Amplifiable vectors are well known in the art. See, for example, Kaufman and Sharp, (1982) Mol. Cell. Biol., 2, 1304-1319 and U.S. Pat. Nos. 4,470,461 and 5,122,464. Such operative linking of a DNA sequence to an expression control sequence includes the provision of a translation start signal in the correct reading frame upstream of the DNA sequence. If the particular DNA sequence being expressed does not begin with a methionine, the start signal will result in an additional amino acid (methionine) being located at the N-terminus of the product. This ensures that the antagonist, once expressed, maintains the core structure.

The proteins produced by a transformed host can be purified according to any suitable method. Such standard methods include chromatography (e.g., ion exchange, affinity and sizing column chromatography), centrifugation, differential solubility, or by any other standard technique for protein purification. For immunoaffinity chromatography, a protein such as Sonic hedgehog may be isolated by binding it to an affinity column comprising antibodies that were raised against Sonic hedgehog, or a related protein and were affixed to a stationary support. Alternatively, affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, mass spectrometry, nuclear magnetic resonance and x-ray crystallography.

B. Production of Antagonists from Full-Length Polypeptides

Fragments of isolated hedgehog protein (e.g., SEQ ID NOS: 2-4) having hedgehog antagonist activity are also produced efficiently using methods known to those of skill in the art. In the methods described more fully in the Examples, functional hedgehog antagonists are generated from intact hedgehog proteins.

Peptides can be specifically cleaved by proteolytic enzymes, including, but not limited to plasmin, thrombin, trypsin, chymotrypsin or pepsin. Each of these enzymes is specific for the type of peptide bond it attacks. Trypsin catalyzes the hydrolysis of peptide bonds in which the carbonyl group is from a basic amino acid, usually arginine or lysine. Pepsin and chymotrypsin catalyse the hydrolysis of peptide bonds from aromatic amino acids, such as tryptophan, tyrosine and phenylalanine. Alternate sets of cleaved protein fragments are generated by preventing cleavage at a site which is susceptible to a proteolytic enzyme. For instance, reaction of the epsilon-amino acid groups of lysine with ethyltrifluorothioacetate in mildly basic solution yields blocked amino acid residues whose adjacent peptide bond is no longer susceptible to hydrolysis by trypsin. Proteins can be modified to create peptide linkages that are susceptible to proteolytic enzymes. For instance, alkylation of cysteine residues with alpha-halo ethylamines yields peptide linkages that are hydrolyzed by trypsin (Lindley, (1956) Nature 178, 647). In addition, chemical reagents that cleave peptide chains at specific residues can be used. For example, cyanogen bromide cleaves peptides at methionine residues (Gross and Witkip, (1961) J. Am. Chem. Soc. 83, 1510). Thus, by treating proteins with various combinations of modifiers, proteolytic enzymes and/or chemical reagents, the proteins may be divided into fragments of a desired length with no overlap of the fragments, or divided into overlapping fragments of a desired length.

C. Chemical Synthetic Methods

Hedgehog antagonists can also be chemically synthesized using techniques known in the art such as the Merrifield solid phase F moc or t-Boc chemistry. Merrifield, Recent Progress in Hormone Research 23: 451 (1967). Examples of prior art methods which allow production and testing of the antagonists are discussed below. These, or analogous methods may be used to make and screen fragments and analogs of an isolated polypeptide (e.g., hedgehog) which can be shown to have biological activity. Hedgehog antagonists can also be created by a combination of chemical and recombinant methods to generate hedgehog chimeras.

D. Production of Other Antagonist DNA and Peptide Sequences

1. Random Mutagenesis Methods

Amino acid sequence variants of the functional hedgehog antagonists containing all or portions of SEQ ID NOS. 2-8 can be prepared by random mutagenesis of DNA which encodes the protein or a particular portion thereof. Useful methods to induce mutations include PCR mutagenesis and saturation mutagenesis. The following examples of such methods are not intended to limit the scope of the present invention, but merely serve to illustrate representative techniques. Persons having ordinary skill in the art will recognize that other methods are also useful in this regard.

PCR Mutagenesis: See, for example Leung et al., (1989) Technique 1, 11-15.

Saturation Mutazenesis: One method is described generally in Mayers et al., (1989) Science 229, 242.

Degenerate Oligonucleotide Mutagenesis: See for example Harang, S. A., (1983) Tetrahedron 39, 3; Itakura et al., (1984) Ann. Rev. Biochem. 53, 323 and Itakura et al., Recombinant DNA, Proc. 3rd Cleveland Symposium on Macromolecules, pp. 273-289 (A. G. Walton, ed.), Elsevier, Amsterdam, 1981.

2. Directed Mutagenesis Methods

Site-directed methods are another way in which an N-terminal cysteine (or a functional equivalent) can be effectively removed to produce the core structure of a functional hedgehog antagonist. Non-random, or directed, mutagenesis provides specific sequences or mutations in specific portions of a polynucleotide sequence that encodes an isolated polypeptide, to provide variants which include deletions, insertions or substitutions of residues of the known amino acid sequence of the isolated polypeptide.

Alanine scanning Mutagenesis: See Cunningham and Wells, (1989) Science 244, 1081-1085).

Oliizonucleotide-Mediated Mutagenesis: See, for example, Adelman et al., (1983) DNA 2, 183. We created a functional antagonist using oligonucleotide-directed mutagenesis by engineering an isolated DNA sequence that encodes a functional antagonist that has a mutation of the N-terminal cysteine to another amino residue, preferably a serine residue (SEQ ID NO: 17: Example 7).

Cassette Mutagenesis: See Wells et al., (1985) Gene 34, 315.

Combinatorial Mutagenesis: See, for example, Ladner et al., WO 88/06630

One of ordinary skill in the art would appreciate that methods exist for generating sets of mutants of the subject antagonist hedgehog proteins, and these methods are especially useful for identifying potential variant sequences (e.g. homologs) that are functional antagonists of the biological activity of hedgehog proteins. In this way, one screens combinatorial libraries containing such sets of antagonist mutants to generate, for example, novel hedgehog homologs which can act as antagonists. Hedgehog homologs can be generated by this approach to act as antagonists, in that they are able to mimic, for As example, binding to patched receptors, yet not induce any biological response, thereby inhibiting the action of authentic hedgehog or hedgehog agonists.

In one aspect of this method, the amino acid sequences for a population of hedgehog antagonists are aligned, preferably to promote the highest homology possible. Such a population of variants can include, for example, hedgehog antagonists from one or more species. Amino acids which appear at each position of the aligned antagonist sequences are selected to create a degenerate set of combinatorial sequences.

In an illustrative embodiment, alignment of the N-terminal approximately 168 residues of the mature protein of each of the known vertebrate hedgehog proteins (i.e., those lacking the first 10 amino acid residues) produces a degenerate set of functional antagonist polypeptides represented by the general formula of SEQ ID NO: 9 wherein each of the degenerate positions "Xaa" in SEQ ID NO: 9 can be an amino acid which occurs in that position in one of the hedgehog proteins, or, to expand the library, each Xaa can also be selected from among amino acid residues which would be conservative substitutions for the amino acids which appear naturally in each of those positions.

For instance, Xaa(6) represents Phe, His or Tyr but may also include Lys, Arg or His; Xaa(7) represents Pro or Ala but may also include Ser, Thr, Tyr, Trp or Phe; Xaa(9) represents any amino acid Lys, Arg or His; Xaa(10) represents Val or Thr but may include Met, Cys, Ser or Thr; and Xaa(11) represents Ala or Val but may include, Leu, Ile, Ser or Thr. Each of the Xaa residues may be represented by those described in SEQ ID NO: 9 or by conservative substitutes, as known by workers having ordinary skill in the art. In an even more expansive library, each Xaa can be selected from any amino acid. There are many ways by which the library of potential hedgehog antagonist homologs described above can be generated. Various techniques are known in the art for screening generated mutant gene products.

Techniques for screening large-gene libraries often include cloning the gene library into replicable expression vectors, transforming appropriate cells with the resulting library of vectors, and expressing the genes under conditions in which detection of a desired activity, e.g., in this case, antagonist activity, or to a downstream intracellular protein, facilitates relatively easy isolation of the vector encoding the gene whose product was detected. Such methods include two hybrid systems in which a hedgehog receptor is used as the "bait" protein and the library of variants of the hedgehog antagonist are expressed as "fish" proteins and various display libraries in which the candidate antagonists are displayed on the surface of a cell or viral particle, and the ability of particular cells or viral particles to bind an appropriate receptor protein via the displayed product is detected in a "panning assay". See, for example, Ladner et al., WO 88/06630; Ladner et al. PCT publication WO 90/02909; Garrard et al., PCT publication WO 92/09690; Marks et al. (1992) J. Biol. Chem. 267:16007-16010; Griffiths et al. (1993) EMBO J 12:725-734; Clackson et al. (1991) Nature 352:624-628; Barbas et al. (1992) PNAS 89:4457-4461), Charbit et al. (1986) EMBO 5, 3029-3037), Schorr et al. (1991) Vaccines 91, pp. 387-392), Agterberg, et al. (1990) Gene 88, 3745, Thiry et al. (1989) Appl. Environ. Microbiol. 55, 984-993); Kuwajima et al. (1988) Bio/Tech. 6, 1080-1083); Hansson et al. (1992) J. Bacteriol. 174, 42394245 and Klauser et al. (1990) EMBO J. 9, 1991-1999); Cull et al. (1992) PNAS USA 89:1865-1869.

F. Other Variants of Isolated Antagonist Polypeptides

Included in the invention are isolated molecules that are: allelic variants, natural mutants, induced mutants, proteins encoded by DNA that hybridize under high or low stringency conditions to a polynucleotide which encodes a polypeptide such as the functional antagonists of this invention. All variants described herein are expected to retain the antagonist biological function. Specifically, a biologically active fragment or analog is one having any in vivo or in vitro activity which is characteristic of the peptides shown in SEQ ID NOS: 5-8 and 11 or which antagonize the biological activity of the hedgehog peptides of SEQ ID NOS. 2-4. Most preferably, the antagonist has at least 10%, preferably 40% or greater, or most preferably at least 90% of the antagonist activity of SEQ ID NOS: 5-8 and 11 in any in vivo or in vitro assay.

Preferred analogs include biologically active antagonist fragments whose sequences differ from the sequences herein by one or more conservative amino acid substitutions or by one or more non conservative amino acid substitutions, or by deletions or insertions which do not abolish the isolated protein's biological activity. Conservative substitutions typically include the substitution of one amino acid for another with similar characteristics such as substitutions within the following groups: valine, alanine and glycine; leucine and isoleucine; aspartic acid and glutamic acid; asparagine and glutamine; serine and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Other conservative substitutions can be readily known by workers of ordinary skill. For example, for the amino acid alanine, a conservative substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine.

Generally, substitutions that may be expected to induce changes in the functional properties of isolated polypeptides are those in which: (i) a polar residue, e.g., serine or threonine, is substituted for (or by) a hydrophobic residue, e.g. leucine, isoleucine, phenylalanine, or alanine; (ii) a cysteine residue (i.e., the N-terminal cysteine and optionally one or more other internal cysteines) is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine.

G. Peptide Mimetics

The invention also provides for generation of mimetics, e.g. peptide or non-peptide antagonist agents. The peptide mimetics are able to antagonize the biological activity of hedgehog protein, for example by disrupting binding of hedgehog to a naturally occurring ligand, e.g., a receptor. The critical residues of a subject antagonist polypeptide which are involved in molecular recognition of a receptor polypeptide or which are involved in its inability to promote hedgehog-dependent signaling, can be determined and used to generate antagonist-derived peptidomimetics (see, for example, "Peptide inhibitors of human papillomavirus protein binding to retinoblastoma gene protein" European patent applications EP412,762A and EP-B31,080A). For example, scanning mutagenesis can be used to map the amino acid residues of a particular antagonist polypeptide involved in its inability to promote hedgehog-dependent signaling, peptidomimetic compounds (e.g. diazepine or isoquinoline derivatives) can be generated which mimic those residues and which therefore can interfere with the function of hedgehog.

Non-hydrolyzable peptide analogs of critical residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), beta-turn dipeptide cores (Nagai et al. (1985) Tetrahedron Lett 26:647)); and Sato et al. (1986) J Chem Soc Perkin Trans 1:1231)), and beta-aminoalcohols (Gordon et al. (1985) Biochem Biophys Res Commun 126:419); and Dann et al. (1986) Biochem Biophys Res Commun 134:71)).

V. Testing for Functional Antagonism

While many bioassays have been used to demonstrate hedgehog activity, the C3H10T1/2 cell line provides a simple system for assessing hedgehog function without the complication of having to work with primary cell cultures or organ explants. The mouse embryonic fibroblast line C3H10T1/2 is a mesenchymal stem cell line that, under defined conditions, can differentiate into adipocytes, chondrocytes, and bone osteoblasts (Taylor, S. M., and Jones, P. A., Cell 17: 771-779 (1979) and Wang, E. A., et al., Growth Factors 9: 57-71 (1993). Bone morphogenic proteins drive the differentiation of C3H10T1/2 cells into the bone cell lineage and alkaline phosphatase induction has been used as a marker for this process (Wang et al., supra). Shh has a similar effect on C3H10T1/2 cells (Kinto, N. et al., FEBS Letts. 404: 319-323 (1997) and we routinely use the alkaline phosphatase induction by Shh as a quantitative measure of its in vitro potency. Shh treatment also produces a dose-dependent increase in gli-1 and ptc-1 expression, which can be readily detected by a PCR-based analysis IV. Uses A. General Generally, the functional hedgehog antagonist proteins described herein are useful in therapeutic, diagnostic and research contexts. By antagonizing the normal biological activity of the hedgehog proteins, the compounds of the present invention can be used in manipulation of tissue, e.g., tissue differentiation, both in vivo and in ex vivo tissue cultures. Such examples may include inhibiting sperm production. Another use is to prevent inhibit growth or differentiation of epithelial cells in a tissue, in particular inhibiting growth of hair on an animal (See Example 8). Also, the antagonists can be used to investigate the role of hedgehog in developmental events, as well as the normal cellular function of hedgehog in adult tissue. Such methods can be used in cell culture but can also be used in the creation of transgenic animals.

In therapeutic applications, the antagonists are used in a manner appropriate to general use and can be formulated in a variety of loads of administration, including systemic and topical or localized administration. Techniques and formulations generally may be found in Remington's Pharmaceutical Sciences, Meade Publishing Co., Easton Pa. For systemic administration, injection is preferred, including intramuscular, intravenous, intraperitoneal and subcutaneous. Liquid solutions of the antagonist can be formulated, preferably in physiologically compatible carrier such as Hanks' solution or Ringer's solution. Lyophilized forms are also included.

In particular, the protein compositions to be used in therapy will be formulated and dosages established in a fashion consistent with good medical practice taking into account the disorder to be treated, the condition of the individual patient, the site of delivery of the isolated polypeptide, the method of administration and other factors known to practitioners. Therapeutic administration of the proteins of this invention is preferably via parenteral delivery, including, subcutaneous, intravenous, intramuscular, intra-articular, intra-synovial, intrasternal, intrathecal, intrahepatic, intralesional and intracranial injection or infusion techniques. Alternative routes include tablets and the like, commercially available nebulizers for liquid formulations, and inhalation of dry powder, lyophilized or aerosolized liposomes. Liquid formulations may be utilized after reconstitution from powder formulations or developed into creams for topical application.

The protein compositions described herein can be administered as a sterile pharmaceutical composition containing a pharmaceutically acceptable carrier, which may be any of the numerous well known carriers, such as water, saline, phosphate buffered saline, dextrose, glycerol, ethanol, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat and the like, or combinations thereof.

The dose administered will be dependent upon the properties of the protein employed, e.g. its binding activity and in vivo plasma half-life, the concentration of the protein in the formulation, the administration route, the site and rate of dosage, the clinical tolerance of the patient involved, the pathological condition afflicting the patient and the like, as is well known within the skill of the physician. Generally, doses of from about $0.5 \times 10-6$ molar or less of protein per patient per administration are preferred, although the dosage will certainly depend on the nature of the protein. Different dosages may be utilized during a series of sequential administrations.

The antagonist polypeptides of the invention may be particularly useful for treating those medical conditions characterized by overexpression of hedgehog protein or, more generally, for treating any condition in which it desired to antagonize the functioning of hedgehog protein. Certain basal cell carcinomas are related to overexpression of hedgehog (Oro et al., (1997), Science 276: 817-821) and certain human tumors e.g., breast carcinomas, medulloblastomas have been found to have an oncogenic mutation in the Shh gene (Epstein et al., U.S. Pat. No. 5,759,811) and antagonists of the present invention would find use in treating such conditions.

As but one example of the application of the proteins of this invention in a therapeutic context, therapeutic antagonists of the invention can be administered to patients suffering from a variety of neoplastic or hyperlastic transformations of cells of the central nervous system. Certain hedgehog proteins may be involved in generation of neuronal tumors. Hedgehog antagonists of the invention, therefore, may be of used in the treatment of, for instance, malignant gliomas, medulloblastomas, neuroectodermal tumors and ependymonas.

Furthermore, the ability of hedgehog protein to regulate neuronal differentiation during development of the nervous system and also presumably in the adult state indicates that antagonists of hedgehog can reasonably be expected to facilitate control of adult neurons with regard to maintenance, functional performance, and aging of normal cells; repair and regeneration processes in lesioned cells; and degeneration and premature death.

The proteins may also be formulated and linked to detectable markers, such as fluoroscopically or radiographically opaque substances, and administered to a subject to allow imaging of tissues. The complexes may also be bound to substances, such as horseradish peroxidase, which can be used as immunocytochemical stains to allow visualization of areas of hedgehog ligand-positive cells on histological sections.

B. Gene Therapy

The isolated polynucleotides of the invention can also be used as a part of a gene therapy protocol to deliver polynucleotides encoding antagonistic form of a hedgehog polypeptide. The invention features expression vectors for in vivo transfection and expression of antagonist polypeptide in particular cell types so as to antagonize the function of hedgehog polypeptide in a cell. Expression constructs of antagonist polypeptides, may be administered in any biologically effective carrier, e.g. any formulation or composition capable of effectively delivering the polynucleotide to cells in vivo.

Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPo_4$ precipitation carried out in vivo.

A preferred approach for in vivo introduction of polynucleotide into a cell is by use of a viral vector containing polynucleotide, e.g. a cDNA, encoding antagonist polypeptide. Infection of cells with a viral vector has the advantage that a large proportion of the targeted cells can receive the polynucleotide. Additionally, molecules encoded within the viral vector, e.g., by a cDNA contained in the viral vector, are expressed efficiently in cells which have taken up viral vector polynucleotide.

A variety of viral vectors can be used as a recombinant gene delivery system for the transfer of exogenous genes in vivo, particularly into humans. These vectors provide efficient delivery of genes into cells, and the transferred polynucleotides can be stably integrated into the chromosomal DNA of the host. For review see Miller, A. D. (1990) Blood 76:271). Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses are well known to those skilled in the art. Examples of suitable packaging virus lines for preparing both ecotropic and amphotropic retroviral systems include Crip, Cre2 and Am. Retroviruses have been used to introduce a variety of genes into many different cell types, including epithelial cells, in vitro and/or in vivo. See for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254: 1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150: 4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573.

Another viral gene delivery system useful in the present invention utilizes adenovirus-derived vectors. See, for example, Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type d1324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells. See Rosenfeld et al, (1992), supra.

Yet another viral vector system useful for delivery of the subject gene is the adeno-associated virus (AAV). Adeno-associated virus is a naturally occurring defective virus that requires another virus, such as an adenovirus or a herpes virus, as a helper virus for efficient replication and a productive life cycle. For a review see Muzyczka et al. Curr. Topics in Micro. and Immunol. (1992) 158:97-129. A variety of polynucleotides have been introduced into different cell types using AAV vectors. See, for example, Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790).

In addition to viral transfer methods, such as those illustrated above, non-viral methods can also be employed to cause expression of antagonist polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject antagonist gene by the targeted cell. Exemplary gene delivery systems of this type include liposomal derived systems, poly-lysine conjugates, and artificial viral envelopes, and tat protein-derived conjugates. See U.S. Pat. No. 5,747, 641. In a representative embodiment, a gene encoding antagonist polypeptide can be entrapped in liposomes bearing positive charges on their surface (e.g., lipofectins) and (optionally) which are tagged with antibodies against cell surface antigens of the target tissue (PCT publication WO91/06309; Japanese patent application 1047381; and European patent publication EP-A-43075).

In clinical settings, the gene delivery systems for the therapeutic antagonist gene can be introduced into a patient by any of a number of methods, each of which is familiar in the art. For instance, a pharmaceutical preparation of the gene delivery system can be introduced systemically, e.g. by intravenous injection, and specific transduction of the protein to target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (U.S. Pat. No. 5,328,470) or by stereotactic injection, e.g. Chen et al. (1994) Proc. Nat. Acad. Sci. USA 91: 3054-3057.

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

The invention will be illustrated by the following, non-limiting Examples.

Example 1

Production of Sonic Hedgehog in *E. coli*

A. Expression in *E. coli*

Human sonic hedgehog N-terminal domain (Shh) protein extending from the N-terminal cysteine of mature sonic hedgehog to amino acid residue 174 in the mature sequence (SEQ ID NO: 3) was subcloned into a pET11d expression vector as a six histidine-tagged fusion protein (histag-Shh) (see SEQ ID NO: 1) with an enterokinase cleavage site engineered into the construct immediately adjacent to the N-terminal cysteine of the mature Shh sequence. This plasmid (containing an ampicillin resistance gene) was transformed into *E coli* strain BL21 (DE3) plysS. In this system, IPTG induces expression fly of T7 RNA polymerase which in turn binds to a T7 promoter region on the transformed plasmid containing the gene of interest. If the target gene products are sufficiently toxic to *E. coli*, this basal level produced by the polymerase can be enough to prevent establishment of the plasmid. A second plasmid plysS (containing a chloramphenicol resistance gene) produces a low level of T7 lysozyme which binds the polymerase and eliminates transcription under noninduced conditions. This system allows plasmids that would be toxic or not otherwise be established to be maintained and expressed. Transformed bacteria were grown to an $A_{550}$ of 0.5 and induced with 1 mM IPTG and grown for a further 2 hours. An aliquot of the culture medium was subjected to SDS-PAGE. The gel was stained with Coomassie blue and the expression level of hedgehog quantified by densitometry. Typical levels of expression were observed where hedgehog represented 4-5% of the total protein. The remainder of the bacteria were collected by centrifugation and stored at −70° C. In the absence of the plysS plasmid, hedgehog expression was poor. No band for hedgehog was detectable by Coomassie blue staining of the lysate when run on SDS-PAGE after induction, indicating that hedgehog expression represented less than 1% of the total protein.

For the purification, all procedures were carried out at 4° C. unless stated. Bacterial pellets from cells expressing Shh at 4-5% of the total protein were thawed, resuspended in lysis buffer (25 mM sodium phosphate pH 8, 150 mM NaCl, 1 mM EDTA, 1 mM PMSF, 0.5 mM DTT) at a ratio of 1:4 (w/v) and lysed by two passes through a Gaulin press (mfg. by APV Rannie, Copenhagen, Denmark) at 12,000 psi. The homogenate was centrifuged at 19,000 g for 60 min and MES 0.5 M pH 5, was added to the resulting lysate at a ratio of 1:10 (v/v).

The lysate at pH 5.5 was loaded onto an SP Sepharose® Fast Flow (Pharmacia, Piscataway, N.J.) column (4 g E. *coli* wet weight/ml resin) previously equilibrated with mM sodium phosphate pH 5.5, 150 mM NaCl. The column was washed with 4 column volumes (CV) of equilibration buffer, then with 3 CV of 25 mM sodium phosphate pH 5.5, 200 mM NaCl, 0.5 mM DTT, and histag-Shh was eluted with 800 mM NaCl in the same buffer. Elution fractions were analyzed for absorbance at 280 nm and by SDS-PAGE. Imidazole (1M stock solution at pH 7) and NaCl (5 M stock solution) were added to a pool of the peak Shh containing fractions from the SP Sepharose® eluate to give final concentrations of 20 mM and 1 M respectively, and this material was loaded onto a Ni-NTA agarose (Qiagen, Santa Clara, Calif.) column (20 mg/ml resin) previously equilibrated with 25 mM sodium phosphate pH 8, 1 M NaCl, 20 mM imidazole, 0.5 mM DTT. The column was washed with 5 CV of the same buffer and histag-Shh eluted with 3 CV 25 mM sodium phosphate pH 8, 1 M NaCl, 200 mM imidazole, 0.5 mM DTT. The protein content in the eluate pool from the Ni column was determined by absorbance at 280 nm. An equal volume of 2.5 M sodium sulfate was added at room temperature to the Ni agarose eluate and this material was loaded onto a phenyl Sepharose® Fast Flow (Pharmacia, Piscataway, N.J.) column (20 mg/ml resin) equilibrated in 25 mM sodium phosphate pH 8, 400 mM NaCl, 1.25 M sodium sulfate, 0.5 mM DTT. Histag-Shh was eluted with 25 mM sodium phosphate pH 8, 400 mM NaCl, 0.5 mM DTT at room temperature. Typically, we recovered 2-3 g of his-tagged Shh from 0.5 kg of bacterial paste (wet weight). The product was filtered through 0.2 μm filter, aliquoted and stored at −70° C. The histagged Shh was about 95% pure as determined by SDS-PAGE. As a further assessment of the characteristics of the purified product, samples were subjected to evaluation by electrospray ionization mass spectrometry (ESI-MS). Approximately 50% of the protein was missing the N-terminal methionine.

ESI-MS data for histag Shh and products resulting after removal of the histag are summarized in Table 1. For MS analysis, aliquots of the purified hedgehog preparations specified were subjected to reversed-phase HPLC on a narrow-bore $C_4$ column (Vydac, catalog #214TP104, 0.46 id×25 cm). Peak fractions were identified by absorbance at 280 nm and infused into a Micromass Quattro II triple quadrupole mass spectrometer equipped with an electrospray ion source. A volume of 6 μl (1 pmol/μl) of HPLC-purified hedgehog was infused directly into the ion source at a rate of 10 μl/min using 50% water, 50% acetonitrile, and 0.1% formic acid as the solvent in the syringe pump. Scans were acquired throughout the sample infusion. All spectral date were acquired and stored in profile mode and were processed using the Micromass Mass Lynx data system. Calculated mass values were determined using average residue masses.

TABLE 1

Characterization of native and truncated Shh variants by ESI-MS

| Protein | Mass (Da) | |
|---|---|---|
| | Calculated | Measured |
| Histag-Shh | | |
| (-Met) | 21433.82 | 21434 |
| (Intact) | 21565.01 | 21565 |
| Sonic hedgehog | 19560.02 | 19560 |
| Indian hedgehog | 19676.1 | 19675 |
| Desert hedgehog | 19733.2 | 19732 |
| Shh (N-10) | 18543.83 | 18544 |
| Shh (N-9/C-3) | 18498.83 | 18498 |
| Shh (N-5) | 19089.47 | 19089 |
| Shh (N-8) | 18828.19 | 18827 |
| Shh (C-9) | 18788.19 | 18789 |
| Shh (C1S) | 19543.96 | 19542 |

To cleave off the six histidine tag, enterokinase (Biozyme, San Diego, Calif.) was incubated with the histag-Shh at an enzyme:Shh ratio of 1:1000 (w/w) for 2 h at 28° C. Uncleaved histag-Shh and free histag were removed by passing the digest through a second Ni-NTA agarose column (20 mg Shh/ml resin). Prior to loading, imidazole (1 M stock solution at pH 7) and NaCl (5M stock solution) were added to the digest to give final concentrations of 20 mM and 600 mM, respectively. This material was loaded onto a Ni-NTA column previously equilibrated in 25 mM sodium phosphate pH 8, 600 mM NaCl, 20 mM imidazole, 0.5 mM DTT and the flow through collected. The column was washed with 1 CV of the same buffer and pooled with the flow through. MES (0.5 M stock solution at pH 5) was added to the Ni agarose unbound fraction to a final concentration of 50 mM and two volumes of water added. This material was loaded onto a second SP Sepharose® Fast Flow column (20 mg/ml resin) equilibrated with 5 mM sodium phosphate pH 5.5, 150 mM NaCl, 0.5 mM DTT. The column was washed with 3 CV of equilibration buffer and 1 CV of the same buffer containing 300 mM NaCl. Shh was eluted with 5 mM sodium phosphate pH 5.5, 800 mM NaCl, 0.5 mM DTT. Atomic absorption data revealed that Shh at this stage contained 0.5 mol equivalent of $Zn^{2+}$. An equimolar concentration of $ZnCl_2$ was added to the Shh eluant and the protein dialyzed against 5 mM sodium phosphate pH 5.5, 150 mM NaCl, 0.5 mM DTT. The resulting Shh was >98% pure as characterized by SDS-PAGE, size exclusion chromatography (SEC) and ESI-MS and by atomic absorption contained between 0.9 and 1.1 $Zn^{2+}$/Shh After removal of the histag and subsequent purification, the purified Shh was shown to have the expected mass as measured by ESI-MS (Table 1). While in preliminary studies we also expressed Shh as a perfect construct without the histag. The expression of Shh was poor and the resulting protein produced was heavily oxidized. As a result, the hedgehog variants that we also expressed in *E. coli* were produced as histag fusions.

Example 2

Testing the Antagonists for Function

Various cell lines have been identified that are responsive to exogenously added hedgehog protein. These responses include the induction of ptc-1 and gli-1 mRNA (Takabatake et al, Febs. Lett. 410: 485-489 (1997)), induction of patched-1 expression (Nakamura et al., Biochem. Biophys. Res. Comm., 237: 465-469, (1997)), phosphorylation of fused (Threond et al., Proc. Nat. Acad. Sci., 93: 4224-4228 (1996), and for selected cell types of the chondrocyte/osteoclast lineage, induction of alkaline phosphatase activity. In the studies described here, we have used the C3H10T1/2 cell line as a reporter for hedgehog signaling. While mature sonic hedgehog was able to bind patched-1 and elicit signaling in the assays described below, a variety of hedgehog variants were identified that bound patched-1 with an affinity similar to mature protein but were inactive in selected functional readouts. These forms of hedgehog were not only inactive by themselves but effectively competed with wild type Sonic hedgehog for function and therefore served as antagonists. Specific examples of such antagonists are described in Examples 3-7.

A. Determination of Alkaline Phosphatase Activity in C3H10T1/2 Cells.

The pluripotent mesenchymal cell line C3H10T1/2 (Reznikoff, C. A., et al., Cancer Research 33, 3231-3238 (1973)) was obtained from the American Type Culture Collection (ATCC) and a tissue culture maintained at 37° C. in Dulbecco's Modified Eagles Medium (DMEM) containing 10% fetal bovine serum (FBS). For assaying AP induction, cells were plated in 96-well plates at 5000 cells/well and 24 hr later, 2-fold serial dilutions of the purified hedgehog protein was added to the medium and incubated for a further 5 days. Cells were then lyzed by incubation for 30 min at 37° C. in 10 mM diethanolamine, pH 9.5, 0.5 mM $MgCl_2$ and assayed for alkaline phosphatase (AP) activity using the chromogenic substrate p-nitrophenylphospate (pNPP) in the same lysing solution. Lysates were incubated with pNPP for 30 min and read at 405 nm in a 96-well plate reader (PerSeptive Biosystems, Framingham, Mass.). AP is a marker for differentiation into the chondrocyte/osteoblast lineage. Typical dose responses for Shh in the C3H10T1/2 assay were observed in the range of 0.1 to 10 µg/ml.

The human, mature Sonic hedgehog (SEQ ID NO: 3) from E. coli that had been expressed as a histagged protein and the histag later removed, was tested for function in the C3H10T1/2 assay with AP activity as a readout. In this assay, Shh produces a dose-dependent response with an $EC_{50}$ of 80 nM and a maximal signal at 250 nM (FIG. 2). This activity can be neutralized with the anti-hedgehog neutralizing mAb 5E1 (data not presented).

Other forms of hedgehog were inactive or showed substantially reduced activity when tested for function in the C3H10T1/2 assay (FIG. 2); including: truncated forms such as human Shh (N-10) (SEQ ID NO: 6, Example 3), rat Shh (N-8) (Example 4), Shh (N-9/C-3) (Example 6), Shh (N-5) (Example 6), Shh (N-8) (Example 6); N terminal modified forms such as C1S Shh (Example 5); and N-terminal extended forms such as histag-Shh (Example 7).

In contrast, a Shh variant ("Shh (C-9)" in Table 1: SEQ ID NO: 10) expressed with only the last 9 residues absent from the C-terminus does not lead to any reduction in C3H10T1/2 activity compared to mature (FIG. 2).

B. Measurement of ptc-1 and gli-1 Induction in C3H10T1/2 Cells by RT-PCR.

Total RNA was prepared by the Trizol method (Chomcyznski, P. and Sacchi, N., Anal. Biochem. 162:156 (1987)). The first strand cDNA was synthesized using murine leukemia virus reverse transcriptase at 37° C. for 45 min. Subsequent amplification was performed by PCR for 27 (ptc-1) or 29 (gli-1) cycles under the following conditions: 95° C. for 3.5 min, annealing at 62° C. for 1 min (patched-1) and 64° C. for 20 sec (gli-1), 72° C. for 1 min (ptc-1) or 20 sec (gli-1). Primer sequences were:

```
Ptc-1
5'-CATTGGCAGGAGGAGTTGATTGTGG-3'   (SEQ ID NO: 12)

5'-AGCACCTTTTGAGTGGAGTTTGGGG-3'   (SEQ ID NO: 13)

Gli-1
5'-CGGGGTCTCAAACTGCCCAGCTT-3'     (SEQ ID NO: 14)

5'-GGCTGGGTCACTGGCCCTC-3'         (SEQ ID NO: 15)
```

Ptc-1 and gli-1 were assessed by detection of PCR products of length 270 bp and 386 bp, respectively. Shh induced ptc-1 and gli-1 RNA with maximal response after 2 days, in which ptc-1 RNA was induced about 2-fold and gli-1 RNA was induced about 5-fold. When the assay was terminated after 5 days, the mRNA levels of both ptc-1 and gli-1 were reduced relative to the levels at 2 days.

C. Induction of Patched-1 Protein in C3H10T1/2 Cell-Based Assay.

C3H10T1/2 cells were grown to confluence in T75 flasks ($3 \times 10^6$ cells) and then incubated with Sonic hedgehog (2 µg/ml) or Shh (N-10)(SEQ ID NO: 6) (2 µg/ml). After 0, 1, 2, 3 or 4 days, the supernatant was discarded and the cells washed with PBS. Cells were lyzed in buffer containing 1% Brij 96 (Sigma Chemical Co., St. Louis Mo.), mM HEPES pH 7.4, 150 mM NaCl, 1 mM EDTA, 1 mM PMSF, 10 µg/ml aprotinin, 10 µg/ml leupeptin, 10 µg/ml o-phenanthroline, 10 mM benzamidine, 10 µg/ml pepstatin A, 0.2 mg/ml sodium vanadate, 4 mg/ml sodium fluoride for 30 min on ice. Lysates were centrifuged for 15 min at 10,000 g and the supernatant incubated with affinity purified rabbit anti-patched-1 antibody and Protein A-Sepharose®.

The immunogen for the antibody was a GST-C terminal murine patched fragment (residues 1237-1414) that had been purified from E. coli construct supplied by Dr. Matt Scott (a gift from Stanford University). The antibody was subjected to two purification steps; first on a non-specific GST resin and second on a GST-patched C terminal resin. After pelleting, beads were washed 5 times with lysis buffer and then boiled 5 min in SDS-containing electrophoresis buffer. Samples were run on a reducing 4-20% SDS-PAGE gel and transferred to nitrocellulose (2 hr at 100V). Blots were probed with anti-patched-1 C-terminal antibody and bands visualized with Protein A-alkaline phosphatase and Pierce ultra supersignal substrate.

Patched protein, $M_r=250,000$, was barely detectable prior to treatment with Shh but showed a dose and time-dependent increase as a result of Shh treatment. Shh induced patched-1 protein with maximal response after 2 days (an approximately 5-fold increase in its expression). After 5 days, the patched protein expression remained elevated, at which point the assay was terminated.

D. Islet-1 Induction Assay.

Intermediate neural plate explants were dissected from the caudal region of stage-10 chick embryos. For the induction of motor neurons, intermediate neural plate explants were embedded in collagen gel, hedgehog protein was added and the explant cultured for 48 hr in N2 medium. Islet-1, a marker for Islet-1+ motor neurons, was detected by an Islet-1 specific monoclonal antibody. Neural plate explants were fixed with 1% paraformaldehyde at 4° C. for 1-3 hr. Explants were incubated with primary antibody overnight at 4° C., with biotinylated anti-mouse IgG overnight at 4° C. and finally with Cy3-conjugated streptavadin overnight at 4° C. The explants were washed and mounted. Explants were examined with a microscope equipped with fluorescence optics and positive nuclei counted.

Shh and truncated variants of Shh were able to induce Isl-1 expression in neural tube explants with comparable dose responses (data not shown). The $EC_{50}$ for Shh and variants Shh N-10, Shh N-9 and Shh N-5 were ~2 nM. This activity in the islet-1 assay is likely to be a generic property of the hedgehog antagonists.

E. Patched-1 Binding Assay.

Human embryonic kidney 293 cells transiently transfected with Myc-tagged patched-1 were used for binding experiments. Direct binding was determined by incubating 293/Patched-1 cells $1\times10^6$/ml) with human Shh-Ig fusion protein (5 nM) (Shh fused in frame after residue 197 to the $F_c$ hinge and of $C_H2$ $C_H3$ portion of human IgG1: Jakubowski et al., Cell Commun. 3: 131-142). Cells were washed and then incubated with phycoerythrin (PE) labeled donkey anti-human IgG. Cells were fixed and read by FACS. For competition binding, Shh or other protein was added at 160 nM and titered down serially 2-fold.

Using a FACS based assay, the apparent $IC_{50}$ for sonic hedgehog N-terminal domain binding to patched-1 was determined to be ~3.5 nM. The truncated variants of Shh (See Table 1) bind with similar affinities (FIG. 4). The C1S antagonist (SEQ ID NO: 8) (See Example 5) binds with a slightly higher affinity (~1 nM).

F. Evaluation of Hedgehog Variants as Antagonists

Samples were tested as antagonists of hedgehog function by evaluating their ability to block wild type Shh function in the C3H 10T1/2 assay. The assay was performed essentially as in Section A of this Example except that all of the test wells received 2 µg/ml of mature Shh in addition to the serial dilutions of the test sample. In the presence of antagonists, reduction in Shh-induced AP activity gives a measure of inhibition so that we assayed inhibition of AP induction as the readout. Data shown in FIG. 3 reveal that all of the hedgehog variants that bind patched-1, but are inactive or have reduced activity in the C3H10T1/2 assay compete with mature Shh and therefore are functional antagonists.

Example 3

Detection of Antagonist from Shh Produced in *Pichia pastoris*

An "N-10" variant missing the first 10 amino acids of human Shh was generated by expression of a construct encoding the N-terminal fragment of mature Sonic hedgehog (SEQ ID NO: 3) in *Pichia pastoris*. All methods and growth media for *Pichia pastoris* are described in Invitrogen product manuals provided by the manufacturer.

Construction of pUB55-1: pUB55 contains the N-terminal domain of human Sonic Hedgehog (SEQ ID NO: 3) with the alpha factor PrePro region as the secretion signal. pUB55 was constructed in pCCM73, a derivative of pPIC9 (obtained from Invitrogen, San Diego, Calif.) with the Kanamycin gene (HincII-HincII fragment) of pUC4-K inserted at the Sph1 site of pPIC9. The human Sonic hedgehog coding sequence from EarI-NotI was obtained from pEAG543 which has a stop codon and NotI site engineered following Gly197 in the coding sequence. Plasmid pCCM73 was cut with XhoI and NotI and was ligated with the EarI-NotI fragment of pEAG543 and Oligonucleotides [5' TCG AGA AAA GAT GCG GAC CGG GCA GGG GGT 3': SEQ ID NO: 18 and 5' CGA ACC CCC TGC CCG GTC CGC ATC TTT TC 3': SEQ ID NO: 19] that form a XhoI-EarI fragment and create the appropriate coding sequence for placing Sonic hedgehog adjacent to the alpha factor leader sequence in frame.

Construction of UB66-1: pUB55.1 was digested with StuI and 10 µg DNA were transformed into *Pichia pastoris* GS115 cells using the methods proscribed by Invitrogen, San Diego, Calif. His⁺ transformants were selected on MD plates, pooled and plated onto YPD/G418 plates to select for multicopy transformants. Strains were grown for two days at 30° C. in 10 ml of BMGY medium, then the cells were resuspended in 2 ml of BMMY medium with 2% methanol and grown for an additional two days at 30° C. Expression was evaluated by SDS-PAGE analysis as described above. Clone UB66-1 was chosen for scaleup and fermentation The transformed yeast were grown for 5 days at 30° C. in a 10 liter fermenter at which point the cells were removed by centrifugation. Expression was in the range 200-400 mg/liter but a substantial portion (>80%) of the protein was proteolysed. After centrifugation, the culture supernatant was diluted with 3 volumes of water and was loaded onto a SP Sepharose® FF column equilibrated with 25 mM sodium phosphate pH 5.4, 150 mM NaCl. The column was subjected to sequential wash steps of 3×1 column volume ("CV") each with 25 mM sodium phosphate pH 5.4, 200 mM NaCl and with 1 CV 25 mM sodium phosphate pH 5.4, 400 mM NaCl.

After washing, a post-translationally clipped variant of Sonic hedgehog ("N-10") (SEQ ID NO: 5) where the first 10 amino acids have been lost due to proteolysis, was eluted with 450 mM NaCl in 25 mM sodium phosphate pH 5.5. Six, 0.5 CV fractions were collected. Intact Sonic hedgehog was eluted with additional steps containing 650 mM and 800 mM NaCl. All of the fractions were characterized by ESI-MS and by SDS-PAGE under reducing and non-reducing conditions. Individual fractions were filtered through a 0.2 µm membrane, aliquoted and stored at −70° C. Fractions 450-1 through 450-3, which contained >90% of the Shh as the N-10 variant, were used in all subsequent studies. ESI-MS data for SEQ ID NO: 5 shown in Table 1 revealed the expected mass. The later-eluting fractions exposed to 450 mM salt contained a mixture of the "N-10" variant and intact Sonic hedgehog.

While mature Shh from *Pichia* was functional in the C3H10T1/2 assay, the N-10 form (SEQ ID NO: 5; "N-10" in Table 1) was inactive in the C3H10T1/2 assay (FIG. 2). When tested for patched-1 binding, the N-10 variant retained its ability to bind patched-1 with an affinity comparable to that for mature Shh. Since the N-10 variant bound patched-1 with mature protein affinity, but was unable to elicit a hedgehog signal in the C3H10T1/2 assay, we reasoned that the protein might act as an antagonist of the mature product. To test this possibility, we performed a competition study with C3H10T1/2 cells, where Shh was added to all wells at a fixed concentration 2.5 µg/ml and eight, 2-fold serial dilutions of the variant were added to the wells, either in a pre-incubation step prior to the addition of intact Shh or directly in the well containing cells at the same time as Shh was added. In the C3H10T1/2 assay, the Shh truncated variant produced in *Pichia* with 10 amino acids absent from the N-terminus ("Shh (N-10)": SEQ ID NO: 5) was able to block induction of AP activity by the mature protein Shh (FIG. 3) with an $IC_{50}$ of ~250 nM.

Example 4

Detection of a Hedgehog Antagonist from Shh produced in Insect Cells

A "N-8" variant of rat Shh-N missing the first 8 N-terminal amino acids was generated by expression of the cDNA encoding rat Shh-N (residues 25-198 in the rat gene sequence) in High Five™ insect cells. Twelve×100 ml cultures of the insect cells grown to a density of 2.4×10⁶ cells/ml in Sf-900 II medium (Life Technologies, Gaithersburg, Md.) were infected with a baculovirus encoding the cDNA of rat Shh-N at a multiplicity of infection of 4 infectious virions per cell. After a 48 h incubation at 28° C., cells were harvested by centrifugation, resuspended in 1.2 liters of 10 mM Na$_2$HPO$_4$ pH 6.0, 150 mM NaCl, 0.5 mM PMSF and harvested by centrifugation. Cells were then resuspended in a further 1.2 liters of 10 mM Na$_2$HPO$_4$ pH 6.0, 150 mM NaCl/0.5 mM PMSF, harvested by centrifugation, and stored at −70° C.

Thawed cells (37.5 g) were resuspended in 300 ml of 10 mM Na$_2$HPO$_4$ pH 6.5, 150 mM NaCl, 0.5 mM PMSF, 5 μM pepstatin, 10 μg/ml leupeptin, 2 μg/ml E64 before 30 ml of 10% Triton X-100 was added. The mixture was incubated on ice for 30 min, whereupon particulates were removed by centrifugation for 10 min at 1500 g.

To the supernatant (330 ml) was added 33 ml of 0.5 M MES (pH 5.0) and the entire sample loaded onto a 37.5 ml (2.5 cm×7.7 cm) column of SP-Sepharose® Fast Flow resin (Pharmacia, Piscataway, N.J.) equilibrated in 5 mM Na$_2$HPO$_4$ pH 5.5, 150 mM NaCl, 0.5 mM PMSF, 0.1% NP-40. Once loaded, the column was washed with 2×37.5 ml aliquots of 5 mM Na$_2$HPO$_4$ pH 5.5, 150 mM NaCl, 0.5 mM PMSF, 0.1% NP-40, followed by 50 ml of 5 mM Na$_2$HPO$_4$ pH 5.5, 300 mM NaCl, 0.5 mM PMSF, 0.1% NP-40.

Bound protein was eluted with 10×12.5 ml of 5 mM Na$_2$HPO$_4$ pH 5.5, 800 mM NaCl, 0.5 mM PMSF, 0.1% NP-40. Fractions containing rat Shh-N (as determined by Western blotting analysis) were pooled (volume=67.5 ml), and mixed with 135 ml of 50 mM Hepes, pH 7.5. The entire sample was then mixed with 3 ml of Sepharose 4B to which the anti-hedgehog monoclonal antibody 5E1 had been coupled at a density of 4.0 mg of antibody per ml of swollen gel. After a 2 h incubation at 4° C., the resin was packed into a column, washed with 10×4.2 ml of phosphate buffered saline pH 7.2, 1% octylglucoside, before rat Shh-N was eluted by washing with 10×1.0 ml aliquots of 25 NaH$_2$PO$_4$ pH 3.0, 300 mM NaCl, 1% octylglucoside into tubes containing 100 μl of 1 M Hepes pH 7.5.

HPLC and ESI-MS analysis of the purified protein indicated that approximately 80% was the N-8 variant, with the remaining 20% being a mixture of full-length protein with myristic-, palmitic-, stearic-, and arachidic acid modifications at the N-terminal cysteine residue. The N-8 variant was separated from the fatty acylated forms by HPLC.

The N-8 form was inactive in the C3H10T1/2 assay and acted as antagonist to block mature Shh activity in the same assay (FIGS. 2 and 3).

Example 5

Production of Antagonists by Direct Expression

A Sonic hedgehog N-terminal domain variant with the N-terminal cysteine mutated to serine ("C1S":SEQ ID NOS: 17 for the DNA) was expressed as a his-tagged protein in *E. coli* and purified and characterized as described above for the mature protein (See Table 1). The C1S variant had reduced activity in the C3H10T1/2 assay (FIG. 2) and served as a functional antagonist for the mature protein. Substitution of the N-terminal cysteine of human Shh with serine (C1S: SEQ ID NO: 8) results in a substantial loss of activity in the C3H10T1/2 assay. The potency (EC$_{50}$) of this antagonist is shifted 3-fold higher in concentration versus mature protein and the maximal AP activity (efficacy) is 3-fold lower. The C1S mutant is also able to block AP induction by human Shh with an IC$_{50}$ of 0.5 mM (data not shown).

In certain instances, it may be worthwhile to delete one or more amino acids from the C-terminus in conduction with other modifications that are used to generate antagonists of the invention. In other instances, amino acid extensions at the C-terminus may be used in the construction of antagonists of the invention. To that end, a polynucleotide encoding a Sonic hedgehog N-terminal domain variant with the last 9 amino acids absent (referred to as "Shh (C-9)": SEQ ID NO: 10) was created and the encoded protein was expressed as a his-tagged protein in *E. coli*, and purified and characterized as described above for the mature protein (See Table 1). SEQ ID NO: 10 had activity comparable to mature protein in the C3H10T1/2 assay (FIG. 2), indicating that the C-terminal sequences in Shh are not critical for function.

Example 6

Proteolytic Generation of Hedgehog Protein Antagonists

Limited proteolysis provides an alternate method for generating Shh antagonists from the mature protein. While many enzymes can be utilized for generating fragments, we successfully have demonstrated this strategy with plasmin, thrombin and enterokinase.

An "N-9/C-3" variant of Shh (SEQ ID NO: 6) lacking amino acids CGPGRGFGK from the N-terminus and residues SGG from the C-terminus was generated by incubation of histag-Shh with bovine plasmin (Sigma Chemical Company. St. Louis, Mo.) in 50 mM Tris-HCl pH 7.4 for 3 hr at 20° C. at a Shh:enzyme ratio of 10:1 (w/w). Plasmin was removed by passing the digest through an ovoinhibitor (Pierce, Rockford, Ill.) column in the same buffer. Uncleaved histag-Shh was removed by passage through Ni-NTA agarose by passing the sample over a column of Ni$^{2+}$ NTA agarose (Qiagen, Santa Clarita, Calif.) in 25 mM Na$_2$HPO$_4$ pH 8.0, 1M NaCl, 20 mM imidazole, 0.5 mM DTT and the remaining protein concentrated by capture/elution on SP Sepharose® FF at pH 5.5 as for mature Shh. Equimolar ZrnCl$_2$ was added to the Shh variants and the proteins dialyzed against 5 mM sodium phosphate pH 5.5, 150 mM NaCl, 0.5 mM DTT. The final products were characterized by ESI-MS (Table 1) and N-terminal sequencing.

An "N-5" variant of Shh (SEQ ID NO: 7) lacking residues CGPGR from the N-terminus was generated by incubation of histag-Shh with biotinylated-thrombin (Novagen, Madison, Wis.) in 50 mM Tris-Cl pH 7.4 for 3 h at 20° C. at a Shh:enzyme ratio of 10:1 (w/w). Biotinylated-thrombin was removed by passing the digest through a streptavadin-agarose column. This N-5 variant was purified and analyzed as described for the N-9/C-3 variant.

An "N-8" variant of Shh (SEQ ID NO: 11) was generated by incubating a mutant form of his-tagged-Shh (in which Gly-8 is replaced by Arg: "G8R-Shh") with enterokinase (Biozyme, San Diego, Calif.) in 25 mM Na$_2$HPO$_4$ pH 8.0, 400 mM NaCl, 0.5 mM DTT for 2 hr at 28° C. at a histagG8R-Shh:enterokinase ratio of 525:1 (w/w). The flow through, containing the intact GSR mutant protein (cleaved at the engineered enterokinase site immediately adjacent to the start of the mature protein) and the N-8 clipped form (cleaved at the C-terminal side of Arg-8), was then subjected to purification on a Biorad® (Hercules, Calif.) Bio-Scale S2 cationic ion exchange column to separate the two forms and to remove the enterokinase. The proteins were eluted with a linear 150 mM-1.0 M NaCl gradient in 5 mM Na$_2$HPO$_4$ pH 5.5, 0.5 mM DTT. The N-8 form eluted from the column at significantly lower NaCl than the intact G8R mutant protein. The N-8 form was dialyzed extensively against 5 mM Na$_2$HPO$_4$ pH 5.5, 150 mM NaCl, 0.5 mM DTT prior to storage at −80° C.

"N-9/C-3" (SEQ ID NO: 6) and SEQ ID NO: 7 ("N-5" in Table 1) are both antagonists that are also inactive in the C3H10T1/2 assay (FIG. 2). The N-9/C-3 (SEQ ID NO: 6) and N-5 (SEQ ID NO: 7) truncated variants of Shh blocked AP activity induced by the mature protein (FIG. 3), both with IC$_{50}$'s of ~80 nM. Addition of control proteins BSA or immunoglobulin isotype G (IgG) did not result in blocking of Shh induction of AP activity (data not presented). The N-9/C-3 truncated variant of Shh (SEQ ID NO: 6) was unable to induce ptc-1 when tested in the assay described in Example 2 (data not presented). These truncated variants of Shh were able to induce Isl-1 expression in neural tube explants with dose responses comparable to those for Shh (data not shown). The EC$_{50}$ for Shh and variants was ~2 nM in the islet-1 conduction assay.

Example 7

Other Antagonists

Substitution of the N-terminal cysteine of human Shh with serine (C1S: SEQ ID NO: 8) results in a substantial loss of activity in the C3H10T1/2 assay as assessed by AP induction (FIG. 2). The potency (EC$_{50}$) of this "C1S" mutant is shifted 3-fold higher in concentration versus wild type. The C1S mutant is also able to block AP induction by human Shh with an IC$_{50}$ of 0.5 mM (data not shown). Certain chemical modifications of the N-terminal cysteine of hedgehog are also expected to generate variants that are antagonists.

Variants of Shh with an N-terminal extension: such as histag-Shh (SEQ ID NO: 1) are inactive in the C3H10T1/2 assay (FIG. 2) and are able to act as antagonists (FIG. 3).

Other hedgehog proteins besides Sonic can act as antagonists in our assays. The N-terminal domain of Indian hedgehog (residues Cys23-197 encoded by the gene sequence) and Desert hedgehog (amino acid residues Cys28-203 encoded by the gene sequence) were also expressed as his-tagged proteins and purified as described above for the Sonic hedgehog protein. The resulting products likewise were greater than 98% pure and ESI-MS data summarized in Table 1 revealed the expected masses for these products.

In the C3H10T1/2 assay, Indian hedgehog is less potent than sonic with an EC$_{50}$~1 mM (FIG. 2). In the same assay, desert hedgehog (Dhh) is inactive. N-terminally truncated versions of Shh produced herein (e.g., "N-9/C-3" and "N-10") are also able to block Ihh activity in the C3H10T1/2 assay (data not shown).

We tested various truncated variants of Indian and Desert hedgehog in the C3H10T1/2 assay. Based on the present disclosure, persons having ordinary skill in the art can now be able to generate truncated versions of Ihh and Dhh (including the same types of truncations as described herein) and also test them in the C3H10T1/2 assay. We expect that such truncated variants of Ihh and Dhh produced in the same manner as we produced truncated versions of Shh are able to block induction of AP activity by the wild type protein Shh and Thh.

Desert hedgehog itself can also act as an antagonist and block Shb or Ihh activity in the C3H10T1/2 assay. The C1S variant, his-tagged Shh, Thh and Dhh all bind to patched receptor with affinities comparable to Sonic hedgehog (FIG. 4). Truncated variants of Thh and Dhh produced in same manner as for sonic would also presumably be able to block induction of AP activity by the Shh or Ihh proteins.

Dhh itself can also act as an antagonist and block Sonic or Indian hedgehog activity in the C3H10T1/2 assay (data not shown). The C1S mutant, histag-Shh, Ihh and Dhh all bind to patched-1 with affinities comparable to Sonic (FIG. 4).

Example 8

Control of Hair Growth Using Hh Antagonists

Hedgehog and its receptor patched (ptc) are expressed in the epithelial and/or mesenchymal cell components of the skin (i.e., the hair follicle) (Iseki et al. (1996) Biochem. Biophys. Res. Comm. 218, 688-693; St-Jaques et al. (1998) Current Biology 8, 1058-1068). The two-way interaction between epithelial and the dermal mesenchymal cells directs the subsequent development of hair follicles. Disrupting this interaction is expected to lead to a modulation of proliferation and/or differentiation events that give rise to hair and/or epithelial tissue structures such as the gut. One can use, for example, hedgehog antagonists such as Shh (N-10) to control growth and differentiation of hair follicle cells. Hair "growth" refers to the formation and elongation of the hair fiber by the dividing cells. Techniques are available and known to test the antagonists of the present invention. One animal model is based on treating pregnant mice with an antagonist of the invention, allowing the antagonist to pass through the placenta into the fetuses and performing various analyses on the embryonic and newborn mice.

Mice were obtained from Jackson Laboratory (Bar Harbor Maine) and Charles River Laboratories. Strains Balb/c and C57bl/6 are used.

A. Blockage of Hair Follicle Morphogenesis in Fetal Mice

Since body coat hair development in mice has been shown to initiate at embryonic day 13.5, E12.5 pregnant mice are injected with antagonist of the invention and control hedgehog which binds hedgehog proteins but does not block the differentiation of 10T1/2 cells are used. Histological analyses is performed on the offspring of the treated and untreated mice. Histological analysis of the mice at development stage E18.5 reveals that the epithelial cell-derived matrix cells undergoes morphogenesis to form the inner root sheath in control mice but that this process is absent in antagonist-treated mice at the same stage and remains delayed throughout the first week of life.

Blockage in Older Fetal Mice

Antagonist proteins of the invention are administered to mice at the stage of the second (3 weeks old) and fourth (9 weeks old) anagen phase of the hair growth cycle. To highlight the effect on hair growth, the backhair of these mice is shaven. The results show that while the backhair of the control mice grows back completely within three weeks, the hair growth in antagonist treated mice is completely blocked.

B. Blockage After Birth

We further demonstrate that hedgehog signaling is required to maintain hair morphogenesis by antagonist administration at later developmental stages. To address this, mice are subjected to antagonist treatment after birth, at which stage the hair follicle morphogenesis has begun. Although there is formation of the bodycoat hair in antagonist-treated mice, the hair is shorter, suggesting a delay of hair growth.

C. Reversal of Blockage

To address whether the hairless phenotype can be reversed by withdrawal of antagonist treatment, such treatments are suspended in some pups which had received antagonist prenatally.

The method provides a means for altering the dynamics of the hair growth cycle to directly inhibit proliferation of hair follicle cells and/or directly modulate differentiation of the stem cells. For example, the method comprises administering to the skin in the area in which inhibition of hair growth is desired an amount of hedgehog antagonist (e.g., Shh (N-10)) sufficient to decrease hair follicle size and/or the rate of hair growth in the animal. Such an affect might be reversible or irreversible.

For instance, the present method can be used in the treatment of trichosis characterized by abnormally rapid or dense growth of hair, e.g. hypertrichosis. Hedgehog antagonists can be used to manage hirsutism, a disorder marked by abnormal hairiness. The subject method can also provide a process for extending the duration of depilation.

Antagonists of the invention can be used to inhibit differentiation of epithelial-derived tissue. Such forms of these molecules can provide a basis for differentiation therapy for the treatment of hyperplastic and/or neoplastic conditions involving epithelial tissue. For instance, the pharmaceutical antagonists of the invention are intended for the treatment of hyperplastic epidermal conditions, such as keratosis, as well as for the treatment of neoplastic epidermal conditions such as those characterized by a high proliferation rate for various skin cancers, as for example basal cell carcinoma or squamous cell carcinoma Hedgehog antagonists can be used for patients undergoing chemo- or radiation-therapies which ordinarily result in hair loss. A hedgehog antagonist will often be cytostatic to epithelial cells, rather than cytotoxic, and such agents can be used to protect hair follicle cells from cytotoxic agents which require progression into S-phase of the cell-cycle for efficacy, e.g. radiation-induced death. By inhibiting cell-cycle progression during such therapies, the subject treatment can protect hair follicle cells from death which might otherwise result from activation of cell death programs. Such treatment by the subject method can provide protection by causing the hair follicle cells to become quiescent. After the therapy has concluded, treatment can also be removed with concomitant relief of the inhibition of follicle cell proliferation.

Other embodiments are within the following claims.

Subject matter disclosed in this application was developed as part of a joint research agreement between Ontogeny, Inc. and Biogen, Inc. Curis, Inc. is the successor in interest to Ontogeny, Inc.

The invention claimed is:

1. A sterile pharmaceutical composition comprising:
   a.) an isolated, functional antagonist of a hedgehog polypeptide, wherein said antagonist can bind to a hedgehog receptor, but does not induce a hedgehog-dependent signaling response, wherein said antagonist is a polypeptide comprising an amino acid sequence represented in any of SEQ ID NOs: 1-8 or 11, and wherein a residue of said antagonist corresponding to Cys-1 of a mature hedgehog polypeptide is deleted; and
   b.) one or more pharmaceutically acceptable carriers.

2. The sterile pharmaceutical composition of claim 1, wherein the antagonist does not induce a hedgehog-dependent signaling response in an assay selected from any of: an alkaline phosphatase induction assay in CH310T1/2 cells; a ptc-1 expression assay in C3H10T1/2 cells; a gli-1 expression assay in C3H10T1/2 cells; or a patched-1 protein induction assay in C3H10T1/2 cells.

3. The sterile pharmaceutical composition of claim 1, wherein the antagonist is missing no greater than about 12 amino acids beginning from a residue corresponding to an N-terminal cysteine corresponding to a Cys-1 of the mature hedgehog polypeptide.

4. The sterile pharmaceutical composition of claim 1, wherein the antagonist has a mutation of the N-terminal cysteine to another amino acid residue.

5. The sterile pharmaceutical composition of claim 4, wherein the another amino acid residue is a serine residue.

6. The sterile pharmaceutical composition of claim 1, wherein the antagonist further includes a modification to a C-terminal end of the antagonist.

7. The sterile pharmaceutical composition of claim 6, wherein the antagonist is missing no greater than about 11 amino acid residues from the C-terminal end as compared to a mature hedgehog polypeptide.

8. The sterile pharmaceutical composition of claim 6, wherein the modification comprises a polypeptide linked to the C-terminal end, the polypeptide having an amino acid sequence unrelated to the antagonist polypeptide.

9. The sterile pharmaceutical composition of claim 8, wherein the polypeptide linked to the antagonist is selected from any of a glutathione-S-transferase, a DNA binding domain, a polymerase activating domain, a histidine tag, or an immunoglobulin or portion thereof.

10. The sterile pharmaceutical composition of claim 6, wherein the C-terminal modification comprises a hydrophobic moiety linked to the C-terminal end.

11. The sterile pharmaceutical composition of claim 1, wherein the Cys-1 of the mature hedgehog polypeptide is selected from any of (a) Cys-1 of a mature Sonic hedgehog polypeptide; (b) Cys-1 of a mature Indian hedgehog polypeptide; or (c) Cys-1 of a mature Desert hedgehog polypeptide.

12. A sterile pharmaceutical composition consisting of (i) a functional antagonist of a hedgehog polypeptide, wherein the antagonist can bind to a hedgehog-responsive receptor, but cannot induce a hedgehog-dependent signaling response, wherein said antagonist is a polypeptide consisting of an amino acid sequence represented in any of SEQ ID NO:s 1-8 or 11, and wherein a residue of said antagonist corresponding to Cys-1 of a mature hedgehog polypeptide is deleted; and (ii) one or more pharmaceutically acceptable carriers.

13. A sterile pharmaceutical composition consisting of (i) a functional antagonist of a hedgehog polypeptide, wherein said antagonist is a polypeptide consisting of an amino acid sequence selected from any of SEQ ID NOS: 5, 6, 7, 9 and 11; and (ii) one or more pharmaceutically acceptable carriers.

14. A sterile pharmaceutical composition comprising:
   a.) an isolated, functional antagonist of a hedgehog polypeptide, wherein said antagonist has the following properties:
      (i) the isolated antagonist binds a hedgehog receptor; and
      (ii) the isolated antagonist blocks alkaline phosphatase (AP) induction by mature hedgehog protein when tested in an AP assay,
   wherein said antagonist is a polypeptide comprising an amino acid sequence represented in any of SEQ ID NOs: 1-8 or 11, and wherein a residue of said antagonist corresponding to Cys-1 of a mature hedgehog polypeptide is deleted and
   b.) a pharmaceutically acceptable carrier.

15. The sterile pharmaceutical composition of claim 14, wherein the hedgehog receptor is patched-1.

16. The sterile pharmaceutical composition of claim 14, wherein said antagonist does not induce ptc-1 and gli-1 expression.

17. The sterile pharmaceutical composition of claim 14, comprising a hedgehog polypeptide lacking an N-terminal cysteine corresponding to Cys-1 of a mature Sonic hedgehog.

18. The sterile pharmaceutical composition of claim 1, wherein a moiety is linked to an amino acid residue of the antagonist, the moiety selected from any of polyethylene glycol and dextran.

19. The sterile pharmaceutical composition of claim 1, wherein the hedgehog-dependent signaling response is measured in a C3H10T1/2 alkaline phosphatase assay.

20. The sterile pharmaceutical composition of claim 1, wherein the antagonist is a polypeptide comprising an amino acid sequence represented in any of SEQ ID NOs: 5, 6, 7, or 11.

21. The sterile pharmaceutical composition of claim 20, wherein the antagonist is a polypeptide comprising an amino acid sequence represented in any of SEQ ID NOs: 5, 6 or 7.

22. The sterile pharmaceutical composition of claim 1, wherein the antagonist is a polypeptide comprising an amino acid sequence represented in SEQ ID NO: 6.

23. The sterile pharmaceutical composition of claim 22, wherein the antagonist is a polypeptide consisting of an amino acid sequence represented in SEQ ID NO: 6.

24. The sterile pharmaceutical composition of claim 12, wherein the antagonist is a polypeptide consisting of an amino acid sequence represented in any of SEQ ID NOs: 5, 6, 7, or 11.

25. The sterile pharmaceutical composition of claim 24, wherein the antagonist is a polypeptide consisting of an amino acid sequence represented in any of SEQ ID NOs: 5, 6 or 7.

26. The sterile pharmaceutical composition of claim 25, wherein the antagonist is a polypeptide consisting of an amino acid sequence represented in any of SEQ ID NOs: 6 or 7.

27. The sterile pharmaceutical composition of claim 13, wherein said antagonist is a polypeptide consisting of an amino acid sequence represented in SEQ ID No: 5.

28. The sterile pharmaceutical composition of claim 13, wherein said antagonist is a polypeptide consisting of an amino acid sequence represented in SEQ ID No: 7.

29. The sterile pharmaceutical composition of claim 13, wherein said antagonist is a polypeptide consisting of an amino acid sequence represented in SEQ ID No: 8.

30. The sterile pharmaceutical composition of claim 13, wherein said antagonist is a polypeptide consisting of an amino acid sequence represented in SEQ ID No: 9.

31. The sterile pharmaceutical composition of claim 13, wherein said antagonist is a polypeptide consisting of an amino acid sequence represented in SEQ ID No: 11.

32. The sterile pharmaceutical composition of claim 1, wherein the antagonist is a polypeptide comprising an amino acid sequence represented in any of SEQ ID NOs: 5, 6, or 7.

33. The sterile pharmaceutical composition of claim 32, wherein the antagonist is a polypeptide comprising an amino acid sequence represented in any of SEQ ID NOs: 5 or 6.

34. The sterile pharmaceutical composition of claim 32, wherein the antagonist is a polypeptide comprising an amino acid sequence represented in any of SEQ ID NOs: 6 or 7.

35. The sterile pharmaceutical composition of claim 12, wherein the antagonist is a polypeptide consisting of an amino acid sequence represented in any of SEQ ID NOs: 5, 6, or 7.

36. The sterile pharmaceutical composition of claim 35, wherein the antagonist is a polypeptide consisting of an amino acid sequence represented in any of SEQ ID NOs: 5 or 6.

37. The sterile pharmaceutical composition of claim 35, wherein the antagonist is a polypeptide consisting of an amino acid sequence represented in any of SEQ ID NOs: 6 or 7.

38. The sterile pharmaceutical composition of claim 1, wherein the pharmaceutically acceptable carrier is selected from the group consisting of: saline, phosphate buffered saline, dextrose, glycerol, ethanol, ion exchangers, alumina, aluminum stearate, lecithin, serum proteins, buffer substances, phosphates, glycine, sorbic acid, potassium sorbate, partial glyceride mixtures of saturated vegetable fatty acids, water, salts, electrolytes, protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, wool fat and any combination thereof.

39. The sterile pharmaceutical composition of claim 1, wherein the pharmaceutically acceptable carrier is a physiologically compatible carrier.

40. A method of making the sterile pharmaceutical composition of claim 1, comprising mixing said isolated functional antagonist with one or more pharmaceutically acceptable carriers under sterile conditions, wherein the functional antagonist is prepared by altering an N-terminal cysteine residue of a mature hedgehog polypeptide from a residue corresponding to residue Cys-1 of mature Sonic hedgehog to a residue that does not correspond to residue Cys-1 of mature Sonic hedgehog.

41. The method of claim 40, wherein the step of altering comprises exposing the hedgehog polypeptide to proteolysis.

* * * * *